US010386365B2

(12) United States Patent
Savoy et al.

(10) Patent No.: US 10,386,365 B2
(45) Date of Patent: Aug. 20, 2019

(54) METHODS FOR DETECTING AND QUANTIFYING ANALYTES USING IONIC SPECIES DIFFUSION

(71) Applicant: Nanohmics, Inc, Austin, TX (US)

(72) Inventors: Steve M. Savoy, Austin, TX (US);
Kyle W. Hoover, Austin, TX (US);
Chris W. Mann, Austin, TX (US);
Daniel R. Mitchell, Austin, TX (US);
Jeremy J. John, Austin, TX (US);
Alexander P. Greis, Austin, TX (US)

(73) Assignee: NANOHMICS, INC., Austin, TX (US)

( * ) Notice: Subject to any disclaimer, the term of this patent is extended or adjusted under 35 U.S.C. 154(b) by 0 days.

(21) Appl. No.: 15/372,343

(22) Filed: Dec. 7, 2016

(65) Prior Publication Data
US 2017/0160227 A1    Jun. 8, 2017

Related U.S. Application Data

(60) Provisional application No. 62/263,773, filed on Dec. 7, 2015.

(51) Int. Cl.
*G01N 33/543* (2006.01)
(52) U.S. Cl.
CPC .............................. *G01N 33/54373* (2013.01)
(58) Field of Classification Search
CPC .............................................. G01N 33/54373
See application file for complete search history.

(56) References Cited

U.S. PATENT DOCUMENTS

| 3,695,848 A | 10/1972 | Taguchi |
| 3,971,065 A | 7/1976 | Bayer |
| 4,542,640 A | 9/1985 | Clifford |
| 5,045,285 A | 9/1991 | Kolesar, Jr. |
| 5,077,210 A * | 12/1991 | Eigler .................... C12N 11/06 435/176 |
| 5,106,756 A | 4/1992 | Zaromb |

(Continued)

FOREIGN PATENT DOCUMENTS

| EP | 0652436 B1 | 3/2002 |
| WO | 0032044 A1 | 6/2000 |

(Continued)

OTHER PUBLICATIONS

Pevzner et al., "Knocking down highly-ordered large-scale nanowire arrays", Nano Lett. vol. 10, pp. 1202-1208, (2010).

(Continued)

*Primary Examiner* — Melanie Brown
(74) *Attorney, Agent, or Firm* — Murphy Strategic IP; George L. Murphy

(57) ABSTRACT

Methods and sensors for detection and quantification of one or more analyte in a test sample are described. A response profile of an ion sensor to a control sample of a known interrogator ion is determined. The ion sensor is exposed to a test sample then to a second sample comprising the known interrogator ion, and a test sample response profile of the ion sensor is determined. One or more test sample sensor response profiles are compared with one or more control sensor response profiles for detecting, identifying, and quantifying one or more analytes in the test sample.

21 Claims, 9 Drawing Sheets

(56) References Cited

U.S. PATENT DOCUMENTS

| | | | |
|---|---|---|---|
| 5,284,570 A * | 2/1994 | Savage | A61B 5/14539 204/403.02 |
| 5,411,709 A | 5/1995 | Furuki et al. | |
| 5,694,932 A | 12/1997 | Michel | |
| 5,807,701 A | 9/1998 | Payne et al. | |
| 5,837,832 A | 11/1998 | Chee et al. | |
| 5,889,196 A | 3/1999 | Ueno et al. | |
| 5,936,730 A | 8/1999 | Foley et al. | |
| 6,010,616 A | 1/2000 | Lewis et al. | |
| 6,028,331 A | 2/2000 | Mastromatteo et al. | |
| 6,238,869 B1 | 5/2001 | Kris et al. | |
| 6,268,222 B1 | 7/2001 | Chandler et al. | |
| 6,277,489 B1 | 8/2001 | Abbott | |
| 6,287,452 B1 | 9/2001 | Allen et al. | |
| 6,327,410 B1 | 12/2001 | Walt et al. | |
| 6,391,562 B2 | 5/2002 | Kambara et al. | |
| 6,426,184 B1 | 7/2002 | Gao et al. | |
| 6,432,360 B1 | 8/2002 | Church | |
| 6,468,657 B1 | 10/2002 | Hou et al. | |
| 6,479,297 B1 | 11/2002 | Sandhu | |
| 6,567,163 B1 | 5/2003 | Sandstrom | |
| 6,638,416 B2 | 10/2003 | Wang et al. | |
| 6,649,403 B1 | 11/2003 | McDevitt et al. | |
| 6,677,606 B1 | 1/2004 | Rajh et al. | |
| 6,689,321 B2 | 2/2004 | Sandhu | |
| 6,787,308 B2 | 9/2004 | Balasubramanian et al. | |
| 6,833,601 B2 | 12/2004 | Murakami | |
| 6,849,166 B2 | 2/2005 | Kita | |
| 6,849,239 B2 | 2/2005 | Morris | |
| 6,872,645 B2 | 3/2005 | Duan et al. | |
| 7,057,168 B2 | 6/2006 | Miller et al. | |
| 7,118,900 B2 | 10/2006 | Seul et al. | |
| 7,129,554 B2 | 10/2006 | Lieber et al. | |
| 7,182,916 B2 | 2/2007 | Noda et al. | |
| 7,211,654 B2 | 5/2007 | Gao et al. | |
| 7,297,497 B2 | 11/2007 | Montagu et al. | |
| 7,301,199 B2 | 11/2007 | Lieber et al. | |
| 7,312,095 B1 | 12/2007 | Gabriel et al. | |
| 7,321,143 B2 | 1/2008 | Kunath et al. | |
| 7,335,153 B2 | 2/2008 | Seul et al. | |
| 7,335,942 B2 | 2/2008 | Edinger et al. | |
| 7,348,184 B2 | 3/2008 | Rich et al. | |
| 7,385,267 B2 | 6/2008 | Lieber et al. | |
| 7,449,757 B2 | 11/2008 | Bradley et al. | |
| 7,460,958 B2 | 12/2008 | Walsh et al. | |
| 7,489,017 B2 | 2/2009 | Patel et al. | |
| 7,491,680 B2 | 2/2009 | Gao et al. | |
| 7,544,638 B2 | 6/2009 | Gao et al. | |
| 7,553,958 B2 | 6/2009 | Gao et al. | |
| 7,575,933 B2 | 8/2009 | Gabriel et al. | |
| 7,786,530 B2 | 8/2010 | Kakoschke et al. | |
| 7,838,466 B2 | 11/2010 | Gao et al. | |
| 7,859,029 B2 | 12/2010 | Lee et al. | |
| 7,948,041 B2 | 5/2011 | Bryant et al. | |
| 8,443,647 B1 | 5/2013 | Kolmakov et al. | |
| 8,450,131 B2 | 5/2013 | Savoy et al. | |
| 8,754,454 B2 | 6/2014 | Bryant et al. | |
| 8,900,517 B2 | 12/2014 | Gabriel et al. | |
| 9,063,053 B2 | 6/2015 | Patolsky et al. | |
| 9,603,560 B2 | 3/2017 | Monty et al. | |
| 9,768,162 B2 | 9/2017 | Savoy et al. | |
| 9,828,696 B2 | 11/2017 | Savoy et al. | |
| 2001/0029049 A1 | 10/2001 | Walt et al. | |
| 2002/0018199 A1 | 2/2002 | Blumenfeld et al. | |
| 2002/0028455 A1 | 3/2002 | Laibinis et al. | |
| 2002/0146745 A1 | 10/2002 | Natan et al. | |
| 2003/0040129 A1 | 2/2003 | Shah | |
| 2003/0065452 A1 * | 4/2003 | Hickman | B82Y 30/00 702/19 |
| 2003/0118595 A1 | 6/2003 | Niemeyer et al. | |
| 2004/0121339 A1 | 6/2004 | Zhou et al. | |
| 2004/0132070 A1 | 7/2004 | Star et al. | |
| 2004/0136866 A1 | 7/2004 | Pontis et al. | |
| 2004/0161370 A1 | 8/2004 | Sunshine et al. | |
| 2004/0248144 A1 | 12/2004 | Mir | |
| 2005/0032060 A1 | 2/2005 | Shah et al. | |
| 2005/0053949 A1 | 3/2005 | Silin | |
| 2005/0065446 A1 | 3/2005 | Talton | |
| 2005/0095649 A1 | 5/2005 | Aebersold et al. | |
| 2005/0130174 A1 | 6/2005 | Yijia et al. | |
| 2005/0142567 A1 | 6/2005 | Su et al. | |
| 2006/0035229 A1 | 2/2006 | Schwarnweber et al. | |
| 2006/0068504 A1 | 3/2006 | Kogi | |
| 2006/0137669 A1 | 6/2006 | Lindner | |
| 2006/0263763 A1 | 11/2006 | Simpson et al. | |
| 2007/0015213 A1 | 1/2007 | Mutz et al. | |
| 2007/0048180 A1 | 3/2007 | Gabriel et al. | |
| 2007/0138007 A1 | 6/2007 | Yemini et al. | |
| 2007/0158547 A1 | 7/2007 | Rich et al. | |
| 2007/0224616 A1 | 9/2007 | Gulari et al. | |
| 2008/0044925 A1 | 2/2008 | Isojima et al. | |
| 2008/0146459 A1 | 6/2008 | Iwakura et al. | |
| 2008/0221806 A1 * | 9/2008 | Bryant | G01N 27/127 702/22 |
| 2008/0293591 A1 | 11/2008 | Taussig et al. | |
| 2008/0312105 A1 | 12/2008 | Bacher et al. | |
| 2009/0018027 A1 | 1/2009 | Ronald et al. | |
| 2009/0036324 A1 | 2/2009 | Fan et al. | |
| 2009/0117571 A1 * | 5/2009 | Solanki | G01N 33/5438 435/6.11 |
| 2009/0153864 A1 | 6/2009 | Kim et al. | |
| 2009/0156427 A1 | 6/2009 | Zhang et al. | |
| 2009/0211437 A1 | 8/2009 | Fleischer et al. | |
| 2011/0071037 A1 | 3/2011 | Muller et al. | |
| 2011/0179852 A1 | 7/2011 | Polonsky et al. | |
| 2012/0178199 A1 * | 7/2012 | Savoy | G01N 27/4148 438/49 |
| 2012/0245055 A1 | 9/2012 | Savoy et al. | |
| 2012/0263922 A1 | 10/2012 | Advincula | |
| 2014/0212979 A1 | 7/2014 | Burgi et al. | |
| 2014/0249052 A1 | 9/2014 | Mehmet et al. | |
| 2014/0332407 A1 * | 11/2014 | Mai | G01N 27/3276 205/777.5 |
| 2017/0160221 A1 | 6/2017 | Savoy et al. | |
| 2017/0160250 A1 | 6/2017 | Savoy et al. | |
| 2017/0343538 A9 | 11/2017 | Savoy et al. | |
| 2017/0363600 A9 | 12/2017 | Savoy et al. | |

FOREIGN PATENT DOCUMENTS

| | | |
|---|---|---|
| WO | 0079243 A1 | 12/2000 |
| WO | 0100876 A1 | 1/2001 |
| WO | 2001000876 A1 | 1/2001 |
| WO | 2002103371 A2 | 12/2002 |
| WO | 2003079401 A2 | 9/2003 |
| WO | 2003095469 A1 | 11/2003 |
| WO | 2003102546 A2 | 12/2003 |
| WO | 2004011672 A1 | 5/2004 |
| WO | 2005030978 A2 | 4/2005 |
| WO | 2005103718 A1 | 11/2005 |
| WO | 20050103718 A1 | 11/2005 |
| WO | 2006113618 A1 | 10/2006 |
| WO | 2006124089 A1 | 11/2006 |
| WO | 2007/082955 * | 7/2007 |
| WO | 2007139849 A2 | 12/2007 |
| WO | 2008027571 A2 | 3/2008 |
| WO | 2008033848 A2 | 3/2008 |
| WO | 2008082713 A2 | 7/2008 |
| WO | 2010135834 A1 | 12/2010 |
| WO | 2012078908 A1 | 6/2012 |
| WO | 2012151306 A2 | 11/2012 |
| WO | 2013008170 A2 | 1/2013 |

OTHER PUBLICATIONS

Stern et al., "Semiconductin nanowire field-effect transistor biomolecular sensors", IEEE Trans. Electron Devices, vol. 55, No. 11, pp. 3119-3130, (2008).

Comini et al., "Metal oxide nanowires as chemical sensors", Materials Today, vol. 13, No. 7-8, pp. 36-44 (2010).

Liu et al, "A Survey on Gas Sensing Technology", Sensors, vol. 12, pp. 9635-9665, (Jul. 16, 2012).

(56) References Cited

OTHER PUBLICATIONS

Fine et al, "Metal Oxide Semi-Conductor Gas Sensors in Environmental Monitoring", Sensors, vol. 10, pp. 5469-5502, (Jun. 1, 2010).
Gao et al, "Light directed massively parallel on-chip synthesis of peptide arrays with t-Boc chemistry", Proteomics, vol. 3, pp. 2135-2141, (2003).
Yoon, "Current Trends in Sensors Based on Conducting Polymer Nanomaterials", Nanomaterials, vol. 2013 (3), pp. 524-529.
Ju et al, "Single-carbon discrimination by selected peptides for individual detection of volatile organic compounds", Scientific Reports, vol. 5, Article No. 9196, pp. 1-6, (Mar. 17, 2015).
Arrieta A et al, "Voltammetric sensor array based on conducting polymer-modified electrodes for the discrimination of liquids" vol. 49, No. 26, pp. 4543-4551, Oct. 15, 2004.
Ghanashyam Acharya et al, "Rapid Detection of S-Adenosyl Homocysteine Using Self-Assembled Optical Diffraction Gratings" vol. 47, No. 6, pp. 1051-1053, Jan. 25, 2008.
Pouthas F et al, "DNA detection on transistor arrays following mutation-specific enzymatic amplification", vol. 84, No. 9, pp. 1594-1596, Mar. 1, 2004.
Arjang Hassibi et al, "A Programmable 0.18-CMOS Electrochemical Sensor Microarray for Biomolecular Detection", vol. 6, No. 6, pp. 1380-1388, Dec. 1, 2006.
Kodoyianni, "Label-free analysis of biomolecular interactions using SPR imaging", Biotechniques vol. 50:(1), pp. 32-40, 2011.
Mohd Azmi et al., "Highly sensitive covalently functionalised integrated silicon nanowire biosensor devices for detection of cancer risk biomarker", Biosensors and Bioelectronics, vol. 52, pp. 216-224, (Sep. 3, 2013).
Lichtenstein et al, "Supersensitive fingerprinting of explosives by chemically modified nanosensors arrays", Nature Communications., vol. 5, pp. 4195-4207, (Jun. 24, 2014).
Xiao et al, "Label-Free Electronic Detection of Thrombin in Blood Serum by Using an Aptamer-Based Sensor", Angew. Chem. Int. Ed., vol. 44, pp. 5456-5459, (2005).
PCT International Searching Authority; International Search Report and Written Opinion of the International Searching Authority issued in PCT Application PCT/US2012/030133, dated Jul. 18, 2012, pp. 1-14.
Park et al, Array-Based Electrical Detection of DNA with Nanoparticle Probes, Science, vol. 295, pp. 1503-1506, (Feb. 22, 2002).
Office Action issued in U.S. Appl. No. 13/070,077, dated Jun. 5, 2012.
Office Action issued in U.S. Appl. No. 13/070,077, dated Aug. 7, 2012.
Office Action issued in U.S. Appl. No. 13/070,077, dated Dec. 26, 2012.
Office Action issued in U.S. Appl. No. 13/070,077, dated Feb. 7, 2013.
Office Action issued in U.S. Appl. No. 13/070,077, dated Apr. 4, 2013.
Office Action issued in U.S. Appl. No. 13/070,077, dated Apr. 23, 2014.
Office Action issued in U.S. Appl. No. 13/070,077, dated Nov. 6, 2014.
Office Action issued in U.S. Appl. No. 13/070,077, dated Mar. 19, 2015.
Office Action issued in U.S. Appl. No. 13/070,077, dated Oct. 20, 2015.
Office Action issued in U.S. Appl. No. 13/070,077, dated May 12, 2017.
Office Action issued in U.S. Appl. No. 13/070,077, dated Jul. 24, 2017.
Samain et al, "Differentiating a Diverse Range of Volatile Organic Compounds with Polyfluorophore Sensors Built on a DNA Scaffold", Chem. Eur. J., vol. 17, pp. 174-183, (Dec. 10, 2010).
Thewes et al, "A CMOS Medium Density DNA Microarray with Electronic Readout", Mater. Res. Soc. Symp. Proc., vol. 869, pp. D3.4.1-D3.4.11, (2005).
Stadler et al, "Multifunctional CMOS Microchip Coatings for Protein and Peptide Arrays", J. Proteome Res., vol. 6, pp. 3197-3202, (Jul. 12, 2007).
Rodrigues et al, "Coating of Solid-Phase Microextraction Fibers with Chemically Bonded Silica Particles: Selective Extraction of Polycyclic Aromatic Hydrocarbons from Drinking Water Samples", J. Chromat. Sci., vol. 40, pp. 489-494, (2002).
Schroder et al, "Addressable Microfluidic Polymer Chip for DNA-Directed Immobilization of Oligonucleotide-Tagged Compounds", Small Jour., vol. 5(13), pp. 1547-1552, (Mar. 26, 2009).
Platt et al, "Aptamer evolution for array-based diagnostics", Anal. Biochem., vol. 390, pp. 203-205, (Apr. 15, 2009).
Pizzoni et al, "Selection of peptide ligands for piezoelectric peptide based gas sensors arrays using a virtual screening approach", Biosensors Bioelectronics, vol. 52, pp. 247-254, (Sep. 4, 2013).
Niemeyer et al, "Combination of DNA-directed immobilization and immuno-PCR: very sensitive antigen detection by means of self-assembled DNA±protein conjugates", Nucl. Acids Res., vol. 31(16), pp. e90, (2003).
McNally et al, Self-assembly of micro- and nano-scale particles using bio-inspired events, Appl. Surf. Sci., vol. 214, pp. 109-119, (2003).
McCauley et al, "Aptamer-based biosensor arrays for detection and quantification of biological macromolecules" Anal. Biochem., vol. 319, pp. 244-250, (2003).
Kozak et al, "Improving the Signal-to-Noise Performance of Molecular Diagnostics with PEG-Lysine Copolymer Dendrons", Biomacromolecules, vol. 10, pp. 360-365, (Jan. 21, 2009).
Li et al, "In2O3 nanowires as chemical sensors", Applied Phys. Letters, vol. 82(10), pp. 1613-1615, (Mar. 10, 2003).
Kong et al, "Nanotube Molecular Wires as Chemical Sensors", Science, vol. 287, pp. 622-625, (Jan. 28, 2000).
Ivanov et al, "Antibodies Immobilized as Arrays to Profile Protein Post-translational Modifications in Mammalian Cells", Molec. Cell. Proteomics, vol. 3.8, pp. 788-795, (May 3, 2004).
Hui, "Guided molecular self-assembly: a review of recent efforts", Smart Mater. Struct., vol. 12, pp. 264-271, (Mar. 27, 2003).
Hatchett et al, "Composites of Intrinsically Conducting Polymers as Sensing Nanomaterials", B Chem. Rev., pp. A-U, (Jan. 3, 2008).
Dandy et al, "Array feature size influences nucleic acid surface capture in DNA microarrays", Proc. Natl. Acad. Sci., vol. 104(20), pp. 8223-8228, (May 15, 2007).
Compagnone et al, "Gold nanoparticles-peptide based gas sensor arrays for the detection of food aromas", Biosensors Bioelectronics, vol. 42, pp. 618-625, (Nov. 22, 2012).
Chhabra et al,"Spatially Addressable Multiprotein Nanoarrays Templated by Aptamer-Tagged DNA Nanoarchitectures", J. Am. Chem. Soc., vol. 129, pp. 10304-10305, (2007).
Bashir, "DNA Nanobiostructures", Materials Today, vol. Nov.-Dec. 2001, pp. 30-39, (2001).
Cao et al, "Silicon Nanowire-Based Devices for Gas-Phase Sensing", Sensors, vol. 14, pp. 245-271, (Dec. 24, 2013).
De Smet et al, "Organic Surface Modification of Silicon Nanowire-Based Sensor Devices", in Nanowires—Implementations and Applications, Dr. Abbass Hashim (Ed.), InTech, Rijeka, Croatia, Ch. 13, pp. 267-288, (Jul. 18, 2011).
Edelstein et al, "The BARC biosensor applied to the detection of biological warfare agents", Biosensors & Bioelectronics, vol. 14, pp. 805-813, (2000).
Galoppini, "Linkers for anchoring sensitizers to semiconductor nanoparticles", Coordination Chemistry Reviews, vol. 248, pp. 1283-1297, (May 28, 2004).
Georgiev et al, "Fully CMOS-compatible top-down fabrication of sub-50 nm silicon nanowire sensing devices", Microelectronic Engineering, vol. 118, pp. 47-53, (Jan. 7, 2014).
Huang et al, "Gas Sensors Based on Semiconducting Metal Oxide One-Dimensional Nanostructures", Sensors, vol. 9, pp. 9903-9924, (Dec. 4, 2009).
Kanan et al, "Semiconducting Metal Oxide Based Sensors for Selective Gas Pollutant Detection", Sensors, vol. 9, pp. 8158-8196, (Oct. 16, 2009).
Kim et al, "Advances and new directions in gas-sensing devices", Acta Materialia, vol. 61, pp. 974-1000, (2013).

(56) References Cited

OTHER PUBLICATIONS

Kim et al, "Direct label-free electrical immunodetection in human serum using a flow-through-apparatus approach with integrated field-effect transistors", Biosensors and Bioelectronics, vol. 25, pp. 1767-1773, (Dec. 29, 2009).

Korotcenkov et al, "Engineering approaches for the improvement of conductometric gas sensor parameters Part 1. Improvement of sensor sensitivity and selectivity (short survey)", Sensors and Actuators B:Chemical, vol. 188, pp. 709-728, (Aug. 7, 2013).

Lund et al, "Label-Free Direct Electronic Detection of Biomolecules with Amorphous Silicon Nanostructures", Nanomedicine, vol. 2(4), pp. 230-238, (Dec. 2006).

McAlpine et al, "Peptide-Nanowire Hybrid Materials for Selective Sensing of Small Molecules", J Am Chem Soc, vol. 130(29), pp. 9583-9589, (Jul. 23, 2008).

Oleinikov et al, "Self-Assembling Protein Arrays Using Electronic Semiconductor Microchips and in Vitro Translation", J Proteome Res, vol. 2, pp. 313-319, (Apr. 5, 2003).

Sakai, "Theory of gas-diffusion controlled sensitivity for thin film semiconductor gas sensor", Sensors and Actuators B:Chemical, vol. 80, pp. 125-131, (2001).

Samain et al, "Polyfluorophores on a DNA Backbone: Sensors of Small Molecules in the Vapor Phase", Angew Chem Int Ed Engl, vol. 49(39), pp. 7025-7029, (Sep. 17, 2010).

Stern et al, "Label-free biomarker detection from whole blood", Nature Nanotechnology, Advance Online Publication, pp. 1-5, (Dec. 13, 2009).

Timmer et al, "Ammonia sensors and their applications—a review", Sensors and Actuators B, vol. 107, pp. 666-677, (Mar. 16, 2005).

Tomchenko et al, "Detection of chemical warfare agents using nanostructured metal oxide sensors", Sensors and Actuators B, vol. 108, pp. 41-55, (2005).

Wang et al, "Metal Oxide Gas Sensors: Sensitivity and Influencing Factors", Sensors, vol. 10, pp. 2088-2106, (Mar. 15, 2010).

White et al, "Solid-State, Dye-Labeled DNA Detects Volatile Compounds in the Vapor Phase", PLoS Biology, vol. 6 (1), pp. 0030-0036, (Jan. 2008).

Zhang et al, "An integrated chip for rapid, sensitive, and multiplexed detection of cardiac biomarkers from fingerprick blood", Biosensors and Bioelectronics, vol. 28, pp. 459-463, (Jul. 18, 2011).

Mascini et al, "Piezoelectric sensors for dioxins: a biomimetic approach", Biosensors and Bioelectronics, vol. 20, pp. 1203-1210, (Aug. 20, 2004).

Wu et al, "Exploring the recognized bio-mimicry materials for gas sensing", Biosensors & Bioelectronics, vol. 16, pp. 945-953, (2001).

Wu et al, "Synthetic peptide mimicking of binding sites on olfactory receptor protein for use in 'electronic nose'", J Biotechnol, vol. 80, pp. 63-73, (2000).

Office Action issued in U.S. Appl. No. 15/372,248, dated Feb. 1, 2018.

Response to Office Action filed in U.S. Appl. No. 15/372,248, filed May 27, 2018.

Office Action issued in U.S. Appl. No. 15/372,248, dated Aug. 27, 2018.

Office Action issued in U.S. Appl. No. 15/372,248, dated Apr. 10, 2019.

Office Action issued in U.S. Appl. No. 15/372,075, dated Apr. 16, 2019.

Wan, Jin et al. "Silicon nanowire sensor for gas detection fabricated by nanoimprint on SU8/SiO2/PMMA trilayer." Microelectronic Engineering 86 (2009):1238-1242.

* cited by examiner

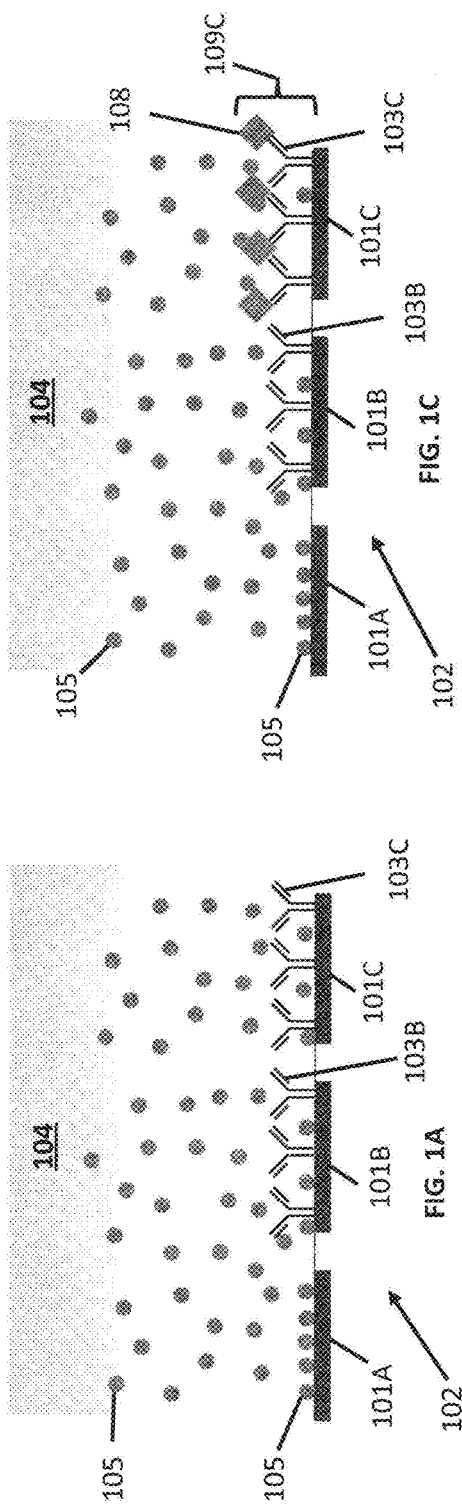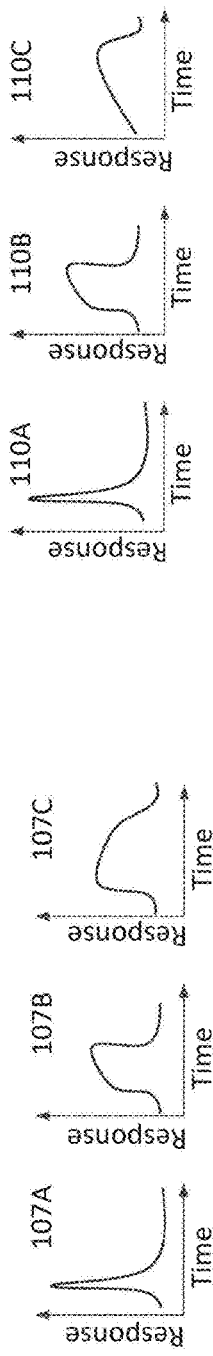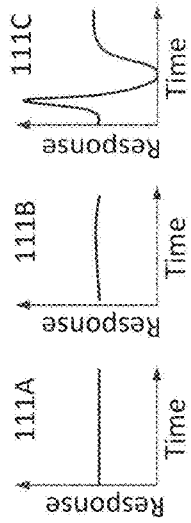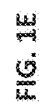

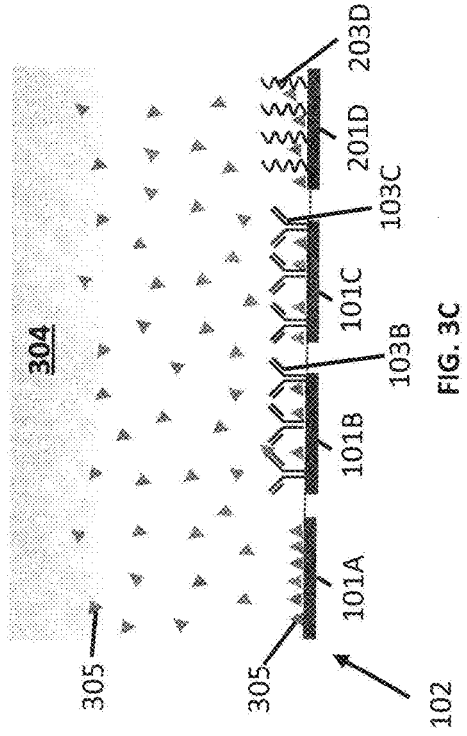
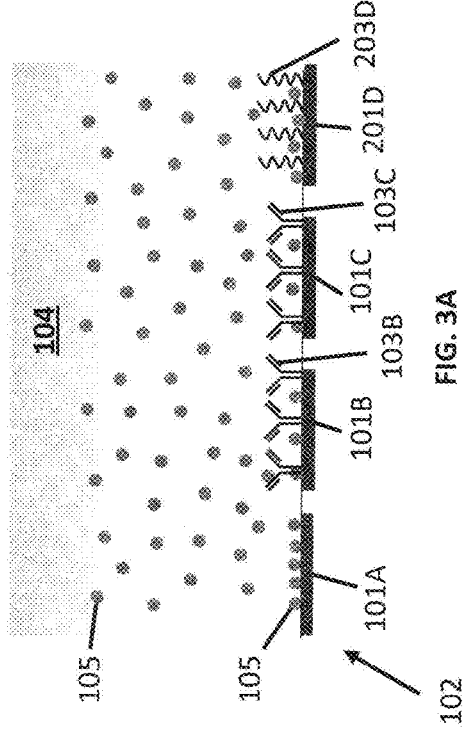
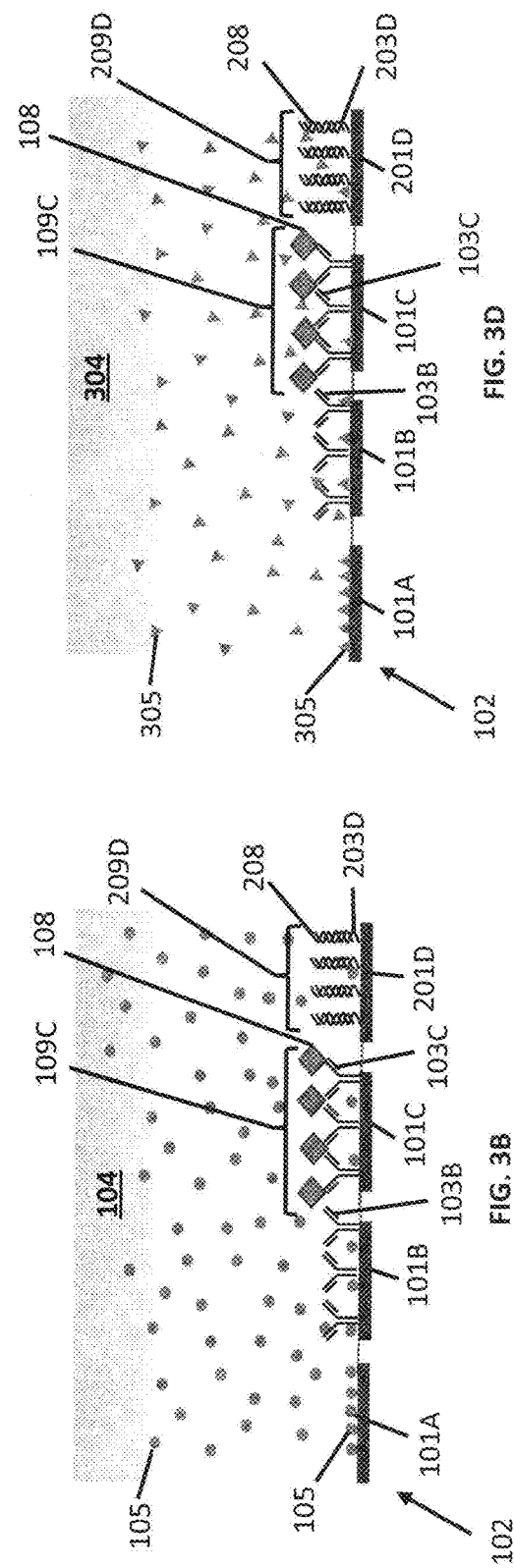

METHODS FOR DETECTING AND QUANTIFYING ANALYTES USING IONIC SPECIES DIFFUSION

This application claims priority under 35 U.S.C. § 119 to U.S. Provisional Application No. 62/263,773 filed Dec. 7, 2015, which is incorporated by reference herein in its entirety.

STATEMENT REGARDING FEDERALLY SPONSORED RESEARCH

The invention was made, in part, with government support under Contract No. W81XWH-14-C-0155 DHP awarded by the U.S Army. The government has certain rights in the invention.

FIELD OF THE INVENTION

The invention is related to analyte detection and quantification. Some applications of the invention include the use of methods and sensors of the invention for detecting the presence of, and quantifying chemicals, biomolecules, and other analytes from biological samples and from other types of samples.

GENERAL DESCRIPTION

Analysis of a test sample for the presence or absence of selected analytes is a useful tool for characterizing the composition of the sample. By way of example only, biomarker and bioanalyte detection and quantification in biological samples are useful for diagnosing disease, monitoring disease progression, detecting pathogens, and genetic profiling. Methods for detection and quantification of biomarkers include the use of fluorescence labeling, the polymerase chain reaction (PCR), and microarrays of nucleic acids. Many biomarker detection systems employ methods for the direct detection of biomolecules following binding of the biomolecule to a complementary binding partner or receptor. Direct detection of biomolecule binding in these systems may employ detection of radioactive-labeled molecules, electrochemical detection, or optical sensors for measuring changes in fluorescence, chemiluminescence, or color. Each of these systems exhibits problems with detection and quantification, which may include excessive complexity, limited sensitivity and specificity of detection, sample incompatibility, and irreproducibility.

Embodiments of the invention include methods, compositions, sensors, and reagents for determining the presence or absence of, and quantifying the amount of an analyte in different types of test samples. In embodiments of the invention, binding of an analyte in a test sample to a complementary binding partner (referred to herein interchangeably as "binder" and "analyte binder") that is present on the surface of an ion sensor results in the formation of a binder-analyte complex. In some embodiments of the invention, methods include exposing an ion sensor derivatized with binders, to a control sample of interrogator ionic solution lacking a complementary analyte, and determining a control ion sensor response profile; exposing an ion sensor derivatized with binders to a test sample that may comprise an analyte that is complementary to the binders; subsequently exposing the ion sensor to a sample of the interrogator ionic solution and determining a test sample ion sensor response profile; comparing the control and test sensor response profiles; and determining the presence or absence of and/or quantity of the analyte in the test sample. A difference between the test sample and control response profiles is indicative of the presence of analyte in the test sample. Different species of ions in ionic solutions may be used in this manner to enhance detection and quantification of analytes. Methods and sensors of the invention thus enable the indirect detection and reproducible and sensitive quantification of one or more analytes in a test sample.

In embodiments of the invention, a response profile of an ion sensor, or an array of sensors, is determined for selected time periods, ranging from a selected time before exposure of a sensor to an interrogator ion sample to a selected time after stopping exposure of a sensor to an interrogator ion sample. In some aspects of the invention, control and test sample sensor response profiles may be determined multiple times with a single type of interrogator ion or with multiple different interrogator ions.

In some embodiments of the invention, multiple ion sensors derivatized with selected different types of binders for binding selected different analytes are used for determining the presence of and/or quantifying a plurality of analytes in a test sample. In specific embodiments of the invention, binders and analytes may be biomolecules, and the test sample may comprise a biological sample. In some aspects of the invention, the analyte is a biomarker. In additional aspects of the invention, binders may be present in a porous matrix on an ion sensor. Binders may be synthesized in situ on an ion sensor or on a porous matrix. Test samples may comprise liquids in some aspects of the invention. In additional aspects of the invention, sensors without binders are used.

In some embodiments of the invention, ion sensors are conductometric semiconducting metal oxide nanosensors. Metal oxide semiconductor type sensors, also known as Taguchi type sensors (U.S. Pat. No. 3,695,848), are capable of rapidly responding to the adsorption of ions on a sensor surface. Fine et al., (2010 Sensors 10:5469-5502), Liu et al., (2012 Sensors 12(7):9635-9665), and Huang et al., (2009 Sensors 9:9903-9924) describe fabrication and operation of Taguchi type sensors and are incorporated by reference herein in their entirety. Absorption or desorption of an ion on the surface of a metal oxide (e.g., $SnO_2$, $ZnO$, $TiO_2$, $In_2O_3$, and $CuO$) changes the conductivity of the metal oxide material allowing for detection and quantification of ion molecules. Metal oxide semiconductor nanosensors and monolithic arrays of semiconducting nanosensors fabricated on the same substrate, such as the imprinted nanotrace nanosensors and arrays described in Savoy et al., (U.S. Patent App. Pub. No. 2012/0178199A1 and U.S. Pat. No. 8,450,131, both of which are incorporated by reference herein in their entirety), are useful in embodiments of the invention. In some aspects of the invention multiple ion sensors are present in an array of sensors.

In embodiments of the invention, comparison of one or more control ion sensor response profiles with one or more test sample sensor response profiles is used to detect, identify, and/or quantify one or more selected analytes present in a test sample. In additional embodiments of the invention, an analyte in the test sample is quantified. Comparisons of control sample and test sample ion sensor response profiles determined under a variety of conditions enable, contribute to, and enhance detection, identification, and quantification of an analyte in a test sample. In some aspects of the invention, one or more control sensor response profiles and test sample sensor response profiles are stored in a database, and comparing sensor response profiles comprises comparing one or more test sample response profiles to one or more control ion sensor response profiles stored in the database. In additional aspects of the invention, deconvolution of ion sensor response data enables the identification and quantification of analytes in a test sample.

In embodiments of the invention, a binder and analyte are complementary and interact in a specific manner. In some aspects of the invention, binders and analytes may be biomolecules, although this is not a requirement of the invention. Test samples for analysis may comprise a biological sample or an environmental sample. Binders useful in embodiments of the invention may be any of numerous types of molecules, compounds, or structures that may be coupled to an ion sensor and that are complementary to an analyte, meaning that the binder is capable of binding to, or otherwise sequestering an analyte in a specific manner.

Other embodiments of the invention are discussed throughout this application. Embodiments described herein are understood to be applicable to all aspects of the invention. It is contemplated that any embodiment discussed herein can be implemented with respect to any method or composition of the invention, and vice versa. Furthermore, compositions of the invention can be used to achieve methods of the invention.

The specification is most thoroughly understood in light of the teachings and references cited within the specification. It should be understood that the drawings, detailed description, and specific examples, while indicating specific embodiments of the invention, are given by way of illustration only, since various changes and modifications within the spirit and scope of the invention will become apparent from this detailed description to those skilled in the art.

Any section headings used herein are for organizational purposes only and are not to be construed as limiting the subject matter described. All documents, or portions of documents, cited in this application, including but not limited to patents, patent applications, articles, books, and treatises, are hereby expressly incorporated by reference in their entirety for any purpose. To the extent publications and patents or patent applications incorporated by reference contradict the invention contained in the specification, the specification will supersede any contradictory material.

BRIEF DESCRIPTION OF THE FIGURES

The following drawings form part of the present specification and are included to further demonstrate certain aspects of the invention. The invention may be better understood by reference to one or more of these drawings in combination with the detailed description of the specification embodiments presented herein.

FIG. 1A-FIG. 1E is a schematic depiction of an exemplary embodiment of the invention for detection of an analyte using ion sensors present on an array of sensors.

FIG. 3A-FIG. 3D is a schematic depiction of an embodiment of the invention showing the interaction of two different types or species of interrogator ions with an array of sensors.

DESCRIPTION OF CERTAIN EXEMPLARY EMBODIMENTS

Figure 2A:
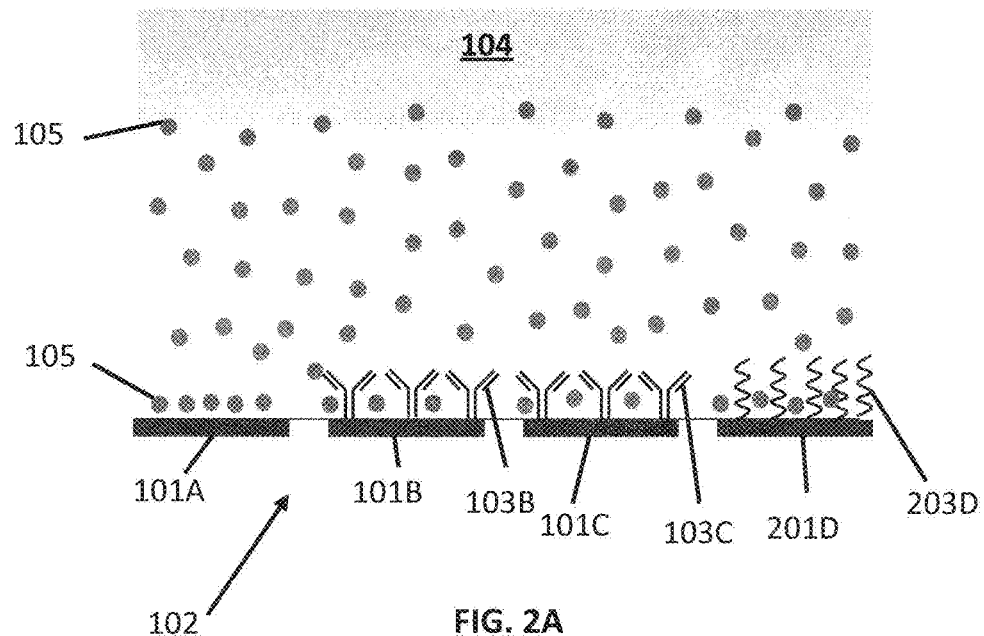
FIG. 2A-FIG. 2B is a schematic depiction of one embodiment of the invention in which an ionic sensor array comprises sensors having different types of biomolecule binders and shows the binder-analyte complexes that are formed upon exposure to a test sample having selected complementary analytes.

Reference will now be made in detail to certain exemplary embodiments of the invention, some of which are illustrated in the accompanying drawings. To assist in understanding the present invention, certain terms are first defined. Additional definitions are provided throughout the application.

The use of the word "a" or "an" when used in conjunction with the term "comprising" in the claims and/or the specification may mean "one," but it is also consistent with the meaning of "one or more," "at least one," and "one or more than one." The use of the term "at least one" in the specification and claims is meant to include "one or more than one", and the use of the term "one or more than one" is meant to include "at least one".

Throughout this application, the term "about" is used to indicate that a value includes the standard deviation of error for the device or method being employed to determine the value.

The use of the term "or" in the claims is used to mean "and/or" unless explicitly indicated to refer to alternatives only or the alternatives are mutually exclusive, although the disclosure supports a definition that refers to only alternatives and "and/or." It is also contemplated that anything listed using the term "or" may also be specifically excluded.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

As used herein, the terms "sensor", "ion sensor", "nanosensor", "ion detector", "detector" and combinations of these are used interchangeably and refer to an ion sensor, or an ion sensor surface that interacts with an ion molecule.

As used herein, the term "analyte" encompasses biomarkers, small molecule metabolites, antigens, proteins, peptides, polypeptides, antibodies, nucleic acids, chemical compounds such as hormones, cytokines, lipids, pharmaceutical compounds (e.g., drugs), sugars, acids, bases, and other molecules or ions that can bind to binders. The presence of one or more analyte in a test sample may be determined, and the amounts of analytes may be quantified using methods and compositions of the invention.

As used herein, the terms "binder" and "analyte binder" refer to biomarkers, biomolecules, small molecule metabolites, simple organic ionophores, macrocyclic ionophores, cytokines, hormones, lipids, proteins, peptides, polypeptides, antibodies, nucleic acids, chemical compounds, pharmaceutical compounds (e.g., drugs), sugars, acids, bases, and other entities that may be present on, or bound, to a detector surface and that are "complementary" to an analyte, meaning that the binder is capable of binding to, or otherwise sequestering, an analyte. The terms "binder-analyte" and "binder-analyte complex" refer to a complex comprising an analyte and binder held together, or bound to, one another. By way of example only, a single-stranded nucleic acid binder will bind in a specific manner with a nucleic acid analyte that is complementary to the nucleic acid binder, forming an analyte-binder complex. Similarly, an antibody binder may recognize and interact in a specific manner with an epitope on a protein analyte and, form an analyte-binder complex. Other specific, complementary interactions between molecules, including biological molecules, are known to those of skill in the art.

In some embodiments of the invention, an ion sensor is derivatized with binders that are anchored to or attached to the ion sensor. Subsequently, exposure of the binder-modified derivatized ion sensor to a test sample comprising an analyte results in binding or sequestration of the analyte by the binder. A solution of known interrogator ions, also referred to herein interchangeably as "interrogator ionic solution", "ionic solution", or "interrogator ions", is then introduced to the sample chamber, and interrogator ions diffuse through the binder-analyte complex to the sensor surface and contact the surface, thereby creating an electrical response based on a change in electrical resistance or conductance of the ion sensor due to interaction of the known interrogator ions with the sensor surface.

In some embodiments of the invention, bound analyte is indirectly detected by a method comprising the steps of (1) exposing an ion sensor derivatized with binders, to a control sample comprising a known interrogator ionic solution and lacking a complementary analyte, and determining a control ion sensor response profile, (2) exposing the binder-derivatized ion sensor to a test sample that may comprise analytes complementary to the binders, (3) after exposing the sensor to the test sample, subsequently exposing the ion sensor to a second sample comprising the interrogator ionic solution and determining a second ion sensor response profile, referred to as a "test sample ion sensor response profile", (4) comparing the control ion sensor response profile and the test sample ion sensor response profile, and (5) determining the presence or absence of and/or quantity of the analyte in the test sample. A difference in the test sample and control sample response profiles is indicative of the presence of analyte in the test sample. In additional embodiments of the invention, comparison of a test sample response profile and a control response profile enables quantification of the analyte in the test sample. Different types of ionic solutions, comprising different ions may be used in this manner to enhance detection and quantification of analytes.

As used herein, "test sample" refers to a sample that is evaluated to determine the presence of, identity of, and/or quantity of one or more analytes in the sample, and "control sample" refers to a sample that comprises at least one known type or species of ion in solution, also referred to as an "interrogator" ionic solution, and that lacks an analyte that is complementary to a binder on the ion sensor.

In embodiments of the invention, an ion sensor response profile is determined for selected time periods, ranging from a selected time before exposure of a sensor to an ion sample to a selected time after stopping ion solution flow. Ion sensor response profiles are determined by measuring a sensor parameter, such as for example resistance, current, capacitance, or electrochemical potential from the selected time before exposure of a sensor to an ionic solution to the selected time after stopping ion solution flow. In embodiments of the invention, the response of an ion sensor to an ion requires interaction of the ion with the sensor surface. In certain aspects of the invention, multiple ion sensor response profiles may be determined and/or recorded in succession, such as for example to record sensor responses to multiple ion exposures. In embodiments of the invention, sensor response profile data may be represented as a plot of sensor response data, e.g., current or resistance vs. time. As used herein, "ion sensor response profile" means the ion sensor response data and associated data determined as described above. "Ion sensor response profile" may also mean a graphical representation or other representation of the determined ion sensor response data and associated data.

In embodiments of the invention, an ion sensor response profile that is determined during exposure of an ion sensor to a control interrogator ionic solution, comprising known ionic species, may be referred to interchangeably as a "control sample ion sensor response profile", a "control sample response profile", a "control sample sensor response profile", or a "control sensor response profile". A "test sample ion sensor response profile", also referred to herein, interchangeably, as a "test sample response profile" or a "test sample sensor response profile" is a sensor response profile that is determined during a second exposure of the sensor to a sample of the known interrogator ionic solution, wherein the second exposure of interrogator ions occurs after exposing the ion sensor to a test sample and allowing for binding of any analyte, which may be present in the test sample, to a binder on the sensor.

As used herein, "exposing" or "exposure of" an ion sensor to an ionic solution sample comprises bringing the ionic solution in proximity to the ion sensor to allow for ions to adsorb to the sensor, such as for example by introducing an ionic solution sample to a chamber in a manner that allows for diffusion of ions to a sensor surface and for adsorption of ions on the sensor surface. The term "exposing" encompasses "contacting". Exposing a sensor to an ionic solution sample encompasses contacting the sample with the sensor and contacting the sensor with the sample.

FIG. 1A-FIG. 1E is a schematic depiction of an exemplary embodiment of the invention for detection of an analyte using ion sensors present on an array of sensors. In this exemplary embodiment (FIG. 1A), ion sensors 101B, 101C are present on ion sensor array 102 and are derivatized with binders 103B, 103C. In some aspects of the invention, no binder is present on a sensor, as illustrated by the underivatized, bare ion sensor 101A. One or more ion sensors on an array may not comprise a binder. Upon exposing the sensors to a control sample comprising a known interrogator ionic solution, interrogator ion species 105 diffuse directly from ionic solution source 104 (in the case of sensor 101A lacking a binder), or through binders 103B and 103C, to sensors 101A, 101B, 101C, whereupon surface-adsorbed ions, or ions otherwise interacting with a sensor, elicit a response by sensors 101, due to a change in electrical conductance of the ion sensors (i.e., an "ion sensor response")

FIG. 1B shows exemplary control sample ion sensor response profiles 107A, 107B, 107C from sensors 101A, 101B, 101C that would be determined following exposure of underivatized ion sensor 101A and the binder-derivatized sensors 101B and 101C to a control sample comprising the interrogator ionic solution (i.e., a solution, with a known concentration of known interrogator ions 105, that does not comprise an analyte). In some embodiments of the invention, response profiles may be determined and recorded as measurements of electric current as a function of time. After stopping ionic solution flow from ionic solution source 104, and optionally purging ions 105 from sensors 101, ion sensor response returns to baseline. Purging may occur by simple diffusion or by introduction of a solution with different ionic concentration including solutions with minimal ionic concentration such as deionized water. Purging may be unassisted or may be accelerated by a heater in contact with sensor array 102.

As depicted in FIG. 1C, sensor array 102 is then exposed to a test sample which may comprise analyte 108 that binds selectively to complementary binder 103C on ion sensor 101C forming binder-analyte complex 109C. In this example, analytes that would bind to binder 103B on ion sensor 101B are not present in the test sample. After exposure of sensors 101 to the test sample, sensor array 102 is exposed a second time to a sample of the interrogator ions 105 from ionic solution source 104, and ions 105 will again diffuse to the surface of sensors 101A, 101B, 101C. Test sample ion response profiles 110A, 110B, 110C are determined after exposure to the test sample and after the formation of binder-analyte complexes 109C (comprising analyte 108 and binders 103C) (FIG. 1D). Ratiometric comparisons of control sample sensor response profiles 107A, 107B, 107C and the corresponding test sample sensor response profiles 110A, 110B, 110C yield ion sensor response profile differentials 111A, 111B, 111C (FIG. 1E) that can be analyzed to determine the presence or absence of an analyte 108 in the test sample. A ratiometric comparison represents the ratio of a control sensor response profile to a test sample sensor response profile or the ratio of a test sample sensor response profile to a control sensor response profile. In some embodiments of the invention in which multiple sensors are used, averaged, normalized sensor response profiles are used for ratiometric comparisons. FIG. 1E schematically depicts that the ratiometric comparison 111C between sensor response profiles 107C and 110C illustrates significant differences between those sensor response profiles. In additional aspects of the invention, further quantitative analysis may be performed to determine the amount of bound analyte 108 in binder-analyte complexes 109 using differential comparative data analytical methods such as principal component analysis and other numerous methods well-known in the art.

In some embodiments of the invention, ion detectors or ion sensors comprise structures having nanoscale dimensions. Exemplary nanoscale structures include nanotubes, nanowires, nanorods, nanofibers, and nanotraces and are referred to generally as "nanostructures". Ion detectors that have nanostructures as ion sensors are also referred to herein as "nanosensors" or "ion nanosensors". Nanostructures have at least one cross sectional dimension, at some point along their length that is less than 1,000 nm (1 micron). In some embodiments of the invention, ion sensors comprise nanostructures having cross-sectional dimensions less than about 500 nm, less than about 250 nm, less than about 100 nm, less than about 50 nm, less than about 10 nm, or less than about 5 nm. In some aspects of the invention, the cross-sectional dimension is from about 0.5 nm to about 1 nm or from about 1 nm to about 5 nm. In some embodiments of the invention, nanostructure lengths range from 1 nm to 100 microns, including any selected size range therebetween. It is specifically contemplated that cross sectional dimensions of nanostructures may be any size in the ranges listed above, including the higher and lower limits listed. All size ranges described are inclusive of the lower and upper limit values. Size ranges within the larger ranges listed above are also contemplated to be useful in some embodiments of the invention. Specific size ranges may be useful in specific aspects of the invention.

In embodiments of the invention, materials useful for ion sensors should be amenable to the attachment or coupling of a binder to the sensor surface in a manner that preserves functionality of the binder for binding a complementary analyte. Desirable materials for use in ion sensors include those that exhibit changes in parameters such as resistance, current, capacitance, or electrochemical potential upon interaction with an ion. Exemplary materials include various forms of semiconducting carbon, conducting polymers, Group IV semiconducting materials, semiconducting oxides, semiconducting nitrides and other transition metal II-VI and III-V semiconductor compounds. In some aspects of the invention, ion sensors comprising one or more of conducting polymers, non-conducting polymers, carbon composites, carbon nanotubes, and gold, or other noble metal catalytic particles may be useful in embodiments of the invention (Savoy et al., U.S. Pat. No. 8,450,131; Hatchett and Josowicz, Chem Rev (2008) 108:746-769; Yoon, Nanomaterials (2013) 3:524-549.).

In some embodiments of the invention, an ion sensor may be a conductometric semiconducting metal oxide ($MO_x$) nanosensor. Mechanisms of ion detection by semiconducting $MO_x$ sensors useful in embodiments of the invention are known in the art. Ion detection by these types of sensors is based on the detection of a resistance change caused by interaction of the sensor surface with ions and charged biomolecules on the surface. Methods and materials for making conductometric semiconducting metal oxide nanotrace sensors using nanoimprint lithography, including materials useful as sensor surfaces and substrates and nanosensor dimensions, are described in Savoy et al., U.S. Pat. No. 8,450,131, which is incorporated by reference herein in its entirety. $MO_x$ nanotrace sensors have greater surface area-to-volume ratios compared to thin films of thin film sensors, permitting rapid interfacial ion exchange compared to diffusion between bulk grain boundaries and enabling the rapid collection of ion sensor response profiles. Furthermore, high surface area-to-volume dimensions can eliminate the need for repeated heat cycling of an ion sensor, which can degrade calibration over time as the grain structure changes. Temperature cycling above ~100° C. can also degrade biomolecules. In other embodiments of the invention, ion sensors may comprise materials other than, or in addition to, semiconducting metal oxides. Although $MO_x$ nanotrace sensors patterned by nanoimprint lithography have advantages in some aspects of the invention, in other aspects of the invention, nanostructure grain dimensions of thin film materials may also be useful as an ion detector. In some embodiments of the invention, methods of the invention may be implemented with sensors that are not nanoscale-dimensioned.

In some embodiments of the invention, ion sensors may be assembled into an array on a substrate. The number of sensors in an array can range from one to hundreds, to thousands, to millions depending on the application and device parameters, such as the number of the read-out circuits. Further embodiments may involve deposition of sensors on the surface of CMOS read-out integrated circuits (ROIC) which may comprise by way of example only, arrays of 3×3, 10×20, 40×60, 320×540, 640×480 VGA, 2056×1560 full size, 2592×3872 10 megapixel, and 3456×5184 18 megapixel. Ion sensors may be configured with aspect ratios of 1×2, 1×3, 1×4, 1×8, 1×32, 1×100, 1×500, 1×1000, 1×10,000, 2×3, 3×4, and 9×16. Sensors may be grouped together in any of a variety of numbers and array sizes and shapes. In some embodiments of the invention, selected nanosensors in an array can be employed as references and controls. There is no limit on the number of ion sensor pixels or the aspect ratio of the sensors in an array 102 of sensors.

In embodiments of the invention, a sensor in an array may be derivatized with any selected type of binder selected for specific interaction with an analyte in a test sample, may be derivatized with linker structures 401, or may be an underivatized, bare sensor. In some aspects of the invention, a single ion sensor or multiple ion sensors are derivatized with a single selected "species" or "type" of binder. In other aspects of the invention, multiple sensors in an array are derivatized with the same selected species of binder. In still other aspects of the invention, multiple sensors in an array on a substrate are each derivatized with selected types of binders. In additional aspects of the invention, multiple sensors derivatized with the same type of binder may be grouped together on a selected region of an array. In still other aspects of the invention, an array of sensors may comprise multiple groups of sensors, each group derivatized with a different, selected type of binder. In certain aspects of the invention, one or more ion sensors may be underivatized sensors. When referring to ion sensors, the terms "underivatized" and "underivatized sensor" mean that the sensor is a bare sensor with no attached molecules. Exemplary methods for arranging nanosensors and groups of nanosensors on an array are described in Savoy et al., U.S. Pat. No. 8,450,131.

In embodiments of the invention, exposing a sensor to a test sample comprises bringing the test sample in proximity to the ion sensor to allow for analyte that may be in the test sample to bind to binder present on the sensor surface. The term "exposing" encompasses "contacting". Exposing a sensor to a test sample encompasses contacting the sample with the sensor and contacting the sensor with the sample. In some embodiments of the invention, exposing a sensor to a test sample comprises introducing a test sample, in a liquid, into a sample chamber with the sensor or passing the sample over a sensor or sensor array. Alternatively, exposing a sensor to a test sample may comprise introducing a stream of gaseous sample into a chamber in contact with a sensor surface. In some aspects of the invention, a test sample suspected of having an analyte of interest, may be allowed to contact an ion sensor (e.g., by incubating the sample with a sensor) for a selected period of time under a selected set of conditions to allow or enhance binding of an analyte to a binder. Liquid samples to be assayed can be of any volume appropriate for the size of the sensor. Sensors are exposed to test samples under physical and chemical conditions effective for achieving binding or other stable interaction of the binder and the complementary analyte. In some aspects of the invention, to enhance formation of specific binder-analyte complexes at different sensors and to prevent or limit non-specific binder-analyte complex formation, it may be necessary to adjust physical or chemical parameters, which may include for example, solution composition (e.g., sample buffer type, pH, salt concentration, and ionic strength), ionic sample composition, length of and temperature of exposure or incubation, number and composition of washes after test sample exposure and prior to exposure with the interrogator ions. These conditions are routinely determinable. In some aspects of the invention, multiple different types of binder-analyte complexes may be capable of forming during a single test sample exposure under the same exposure conditions. In other aspects of the invention, it may be advantageous or necessary to expose an array of sensors having different types of binders to a test sample under a variety of different exposure conditions, for example by sequentially exposing the array of sensors to a test sample. After incubation, the sensors can optionally be treated (e.g., washed) to remove unbound sample components, using conditions that are determined empirically to leave specific interactions intact, but to remove non-specifically bound material. For example, samples can be washed between about one or ten times or more under the same or somewhat more stringent conditions than those used during formation of the binder-analyte complex.

Figure 2B:
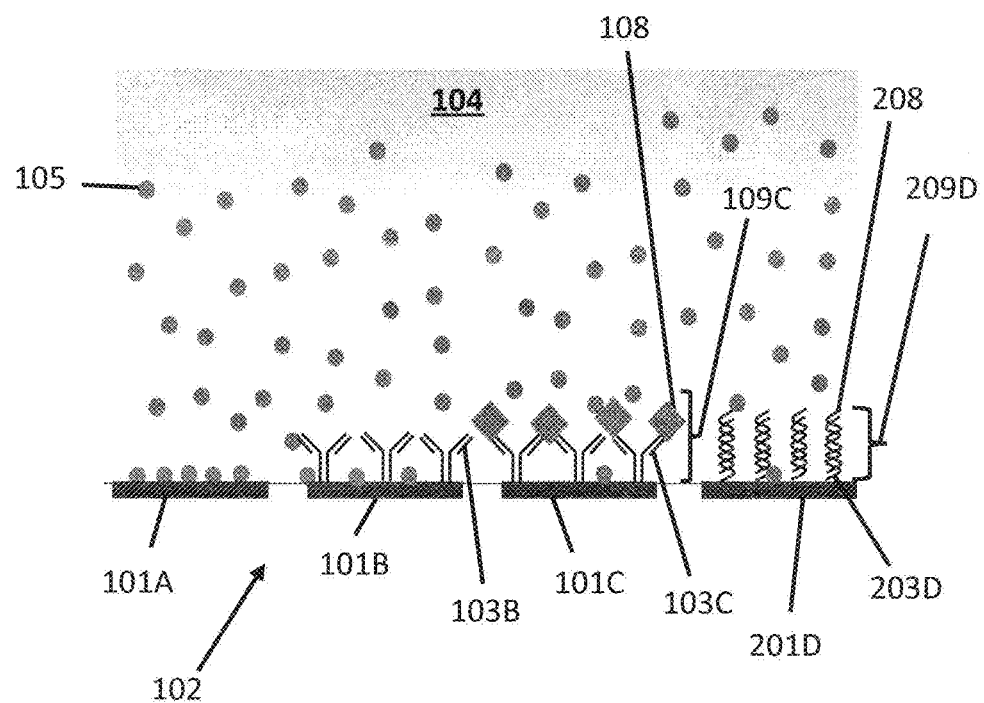

FIG. 2A-FIG. 2B is a schematic depiction of one embodiment of the invention in which an ion sensor array comprises sensors having different types of biomolecule binders and shows the binder-analyte complexes that are formed upon exposure to a test sample having selected complementary analytes. In this exemplary embodiment, in addition to antibody binders 103B, 103C coupled to sensors 101B and 101C respectively (FIG. 2A), a nucleic acid binder 203D is shown coupled to sensor 201D. During exposure of sensor array 102 to a test sample comprising analyte 108, as shown in FIG. 2B, binder-analyte complex 109C forms. If present in the test sample, analyte 208 and binder 203D will also form binder-analyte complex 209D. In this exemplary aspect of the invention, analyte 208 is a nucleic acid that is complementary to nucleic acid binder 203D such that analyte-binder complex 209D is formed (FIG. 2B) during exposure to the test sample.

FIG. 3A-FIG. 3D is a schematic depiction of an embodiment of the invention showing the interaction of two different types or species of interrogator ions with an array of sensors. In some embodiments of the invention, as illustrated in FIG. 3A and FIG. 3B, sensors 101A, 101B, 101C, 201D that are assembled as an array 102 may be exposed to a single type of ion 105 from ionic solution source 104. In other aspects of the invention, as shown in FIG. 3C and FIG. 3D, sensors 101, 201 may be additionally exposed to a different type of interrogator ions 305 from a different ionic solution source 304. Interaction of interrogator ions 105, in a control ionic solution sample having no analyte, with sensors 101, 201 (as depicted in FIG. 3A) will result in control sensor response profiles that are different from the control sensor response profiles produced when interrogator ions 305, in a control ion sample having no analytes, interact with sensors 101, 201 (FIG. 3C). Similarly, after exposure of sensor array 102 to a test sample containing analytes 108 and 208 and formation of binder-analyte complexes 109C and 209D, subsequent exposure of ion sensors 101, 201 to interrogator ions 105 (FIG. 3B) will result in test sample response profiles that are different from the test sample response profiles produced when the sensors are subsequently exposed to interrogator ion molecules 305 (FIG. 3D). Ion sensor response profile differentials (not shown for FIG. 3, but determined as for those shown in FIG. 1E) between control sensor response profiles and test sample sensor response profiles will be different with each different type of interrogator ion used and in some aspects of the invention may provide additional means for determining the presence of and quantification of analytes in a test sample.

Differences in test sample sensor response profiles and control sensor response profiles are observed when analytes are present in a test sample and form binder-analyte complexes 109 and 209 on sensors 101C and 201D, respectively.

Figure 4A:
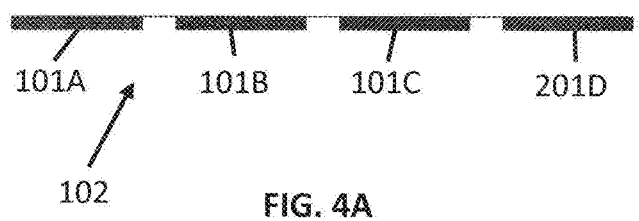
FIG. 4A-FIG. 4C is a schematic depiction of one embodiment of the invention for covalently anchoring binders to ion sensors present as an array of sensors.
Figure 4B:
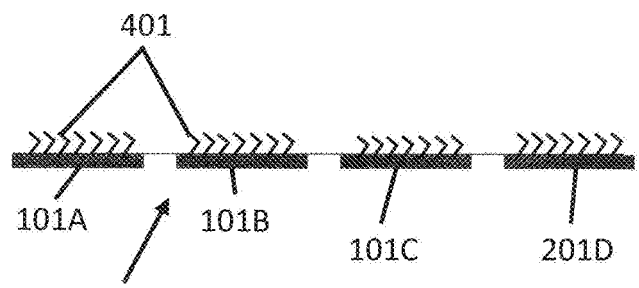
Figure 4C:
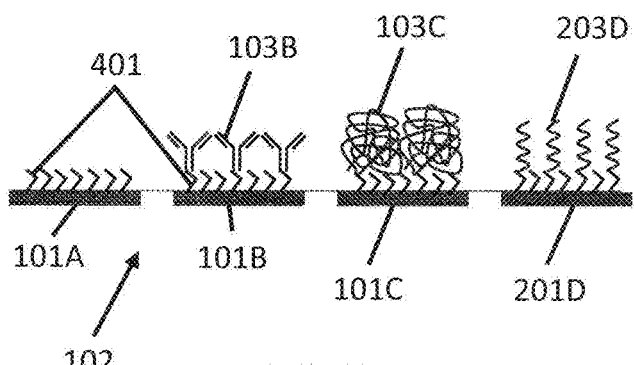

FIG. 4A-FIG. 4C is a schematic depiction of one embodiment of the invention for covalently anchoring binders to ion sensors present as an array of sensors. In this exemplary embodiment, ion sensors 101A, 101B, 101C, 201D, present on ion sensor array 102 (FIG. 4A) are initially derivatized with linker structures 401 on their surfaces as depicted in FIG. 4B. In some aspects of the invention, linker structures 401 may facilitate the attachment of binders, 103B, 103C, 203D to a nanosensor and/or the synthesis of binders directly on the sensor (FIG. 4C). In some aspects of the invention, coupling of binders to linkers is mediated by chemisorption, and in other aspects of the invention coupling is mediated by physisorption. Heterobifunctional linker structures useful for covalent attachment of chemical and biological structures to surfaces are known and commercially available (e.g., from Sigma-Aldrich Co. LLC, St. Louis, Mo., USA). Exemplary linker structures 401 include silanes, glutaraldehydes, succinimides, carboxylates, epoxies and phosphonates to name only a few. In other aspects of the invention, no binder is present on a sensor surface, as illustrated by ion sensor 101A in FIG. 4B and FIG. 4C, having only linker structures 401.

In some embodiments of the invention, it is specifically contemplated that a binder is not a biomolecule. Binders for use in additional embodiments of the invention include biomolecules, biomarkers, small molecule metabolites, cytokines, hormones, lipids, proteins, peptides, polypeptides, antibodies, nucleic acids, aptamers, polymers, chemical compounds, organic compounds, pharmaceutical compounds (e.g., drugs), or other entities that are covalently linked to, synthesized on, or otherwise coupled to a detector surface and that are "complementary" to an analyte, meaning that the binder is capable of binding to, or otherwise sequestering an analyte in a specific manner. In some specific aspects of the invention, binders may be synthetic ionophores that selectively interact with specific types of ions in ionic solutions for example macrocyclic organic molecules in the family of crown eithers, cryptands, and calixarenes. Some ionophores are simple organic molecules that are not macrocyclic (e.g. carbonyl cyanide-p-trifluoromethoxyphenylhdrazone or phenols, urea, and thioureas).

In some aspects of the invention, a binder is a cell or a part thereof, such as by way of example only, a cell membrane or a fragment thereof, a liposome, a nucleus, an organelle, a protein, a receptor molecule, or another subcellular component. Binders may be isolated from cells or may be synthetically prepared. Methods for in vitro synthesis of small molecules, antibodies, peptides, nucleic acids, cell membranes, membrane mimics, liposomes, and other biological and chemical structures are known in the art.

In some embodiments of the invention, binder 103, 203 is synthesized in situ on a nanosensor, with or without linkers. In some aspects of the invention, binders may be peptides 103C or nucleic acids 203D that are synthesized in situ on the nanosensor. In certain aspects of the invention, peptides synthesized on a nanosensor surface may comprise, at least 2, 3, 4, 5, 6, 7, 8, 9, 10, 15, 20, 25, 30, 35, 40, 45, 50, 60, 70, 80, 90, or 100 amino acids or any number therebetween and inclusive of the smaller and larger sizes listed. In other aspects of the invention, peptide length is not limited and may be any length that retains functionality as an analyte binder and that can be synthesized on, or attached to, the surface of nanosensor. Similarly, in certain aspects of the invention, nucleic acids synthesized on a nanosensor may comprise, at least 2, 3, 4, 5, 6, 7, 8, 9, 10, 15, 20, 25, 30, 35, 40, 45, 50, 60, 70, 80, 90, or 100 nucleotides or any number therebetween and inclusive of the smaller and larger sizes listed. In other aspects of the invention, nucleic acid length is not limited and may be any length that retains functionality as an analyte binder and that can be synthesized on, or attached to, the surface of a nanosensor. Representative methods for synthesizing peptides and nucleic acids on surfaces can be found in Gao et al., (Proteomics, (2003) 3:2135-2141), and Gao et al., (U.S. Pat. No. 6,426,184), both of which are incorporated by reference herein in their entirety. Other synthesis methods are known to those with skill in the art.

In other embodiments of the invention, binders are spotted onto an ion sensor. Peptide, protein, and nucleic acid binders useful for spotting onto a nanosensor are typically not limited by size, length, shape, or sequence as long as they can be spotted onto the sensor and bind specifically to or sequester an analyte.

In additional embodiments of the invention, other methods may be used to position binders on sensors 101, 201. Binders may be confined in or otherwise coupled to a porous support matrix on the ion sensor surface, or may be confined in or otherwise coupled to a porous matrix then positioned, or registered to a sensor surface.

Figure 5A:
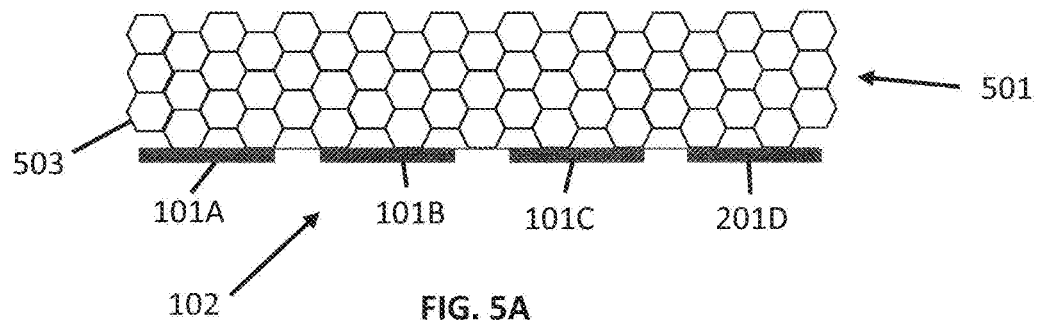
FIG. 5A-FIG. 5C is a schematic depiction of an exemplary embodiment of the invention in which an ion sensor array comprises sensors having multiple biomolecule binder types coupled to a porous matrix present on ion sensors in a sensor array.
Figure 5B:
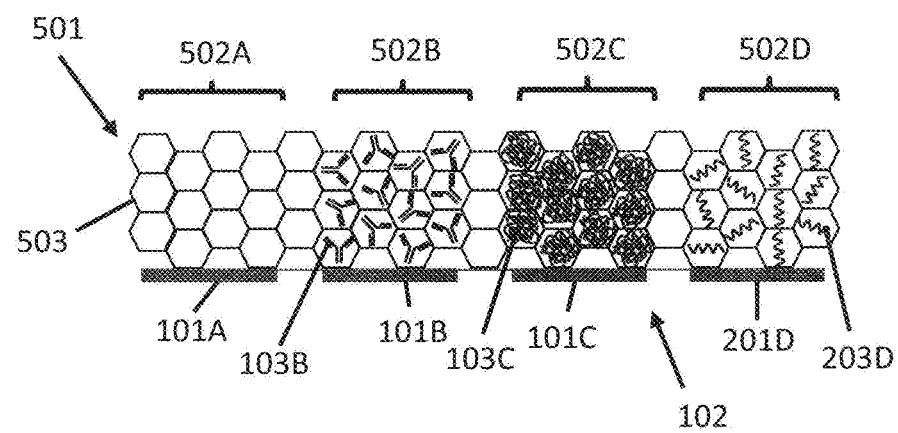
Figure 5C:
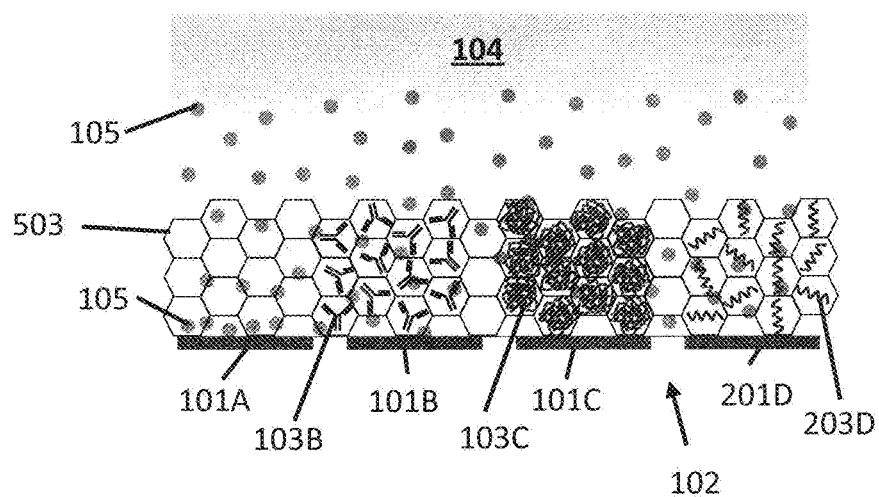

FIG. 5A-FIG. 5C is a schematic depiction of an exemplary embodiment of the invention in which an ion sensor array comprises sensors having multiple biomolecule binder types coupled to a porous support matrix present on ion sensors in a sensor array. FIG. 5A shows an exemplary embodiment of the invention in which a porous support matrix 501, also referred to herein as "porous matrix", is first deposited on sensor array 102. Binders 103, 203 are dispensed onto and/or dispersed into selected regions 502B, 502C, 502D of deposited porous support matrix 501 and subsequently coupled to the porous matrix (FIG. 5B). In some embodiments of the invention, binders are dispensed to deposited porous support matrix 501 that is present on selected sensors so that selected types of binders are in registration with selected sensors of sensor array 102. Numerous methods may be used for dispensing, dispersing, and coupling binders to, or for directly synthesizing binders on, deposited porous support matrix 501. Some exemplary methods include spotting, inkjet printing, drop-casting, silk-screen printing, gravure printing, and flexographic printing. In some aspects of the invention, binders are dispensed to deposited porous support matrix 501 using a bioink.

In some embodiments of the invention, covalent coupling of binders to porous support matrix 501 may be employed to couple the binders to structural segments 503 of porous support matrix 501. By way of example only, covalent coupling to structural segments 503 may be mediated by one or more of numerous anchoring chemistries well known in the art, such as silane heterobifunctional crosslinkers, succinimides, glutaraldehyde, and epoxies. Other types of structures for coupling binders to structural segments 503 of deposited porous matrix 501 include silanes, peptides, nucleotides, carbohydrates, and phosphonates to name only a few. Covalent coupling yields binders permanently attached to deposited porous support matrix 501. In some aspects of the invention, coupling of binders to porous support matrix 502 is mediated by chemisorption, such as for example by covalent coupling, and in other aspects of the invention coupling is mediated by physisorption.

In certain aspects of the invention, materials used for porous support matrix 501 have a high surface area for coupling binders. Porous matrix 501 may comprise biomolecules, crosslinked biomolecules, non-biological material, or mixtures thereof that contain an interconnected network of volumetric space. In some aspects of the invention, structural segments 503 of deposited porous matrix 501 comprise glass, polymer, or composite fibers and may form a mat or sheet. Fibers may be woven or may form a random matrix. In additional aspects of the invention, deposited porous support matrix 501, may comprise beads. In some aspects of the invention, the porosity and thickness of porous matrix 501 may be adjusted and may alter the traversal of the matrix by ions 105 from source 104 prior to the adsorption of ions on the surface of sensor 101A, 101B, 101C, and 201D (FIG. 5C) thereby affecting a control sample or test sample ion sensor response profile. In some aspects of the invention, no binders are dispensed to porous matrix 501, such as in region 502A over select sensor surface 101A (FIG. 5B). In this exemplary aspect of the invention, sensor 101A is derivatized only with porous support matrix 501.

Figure 6A:
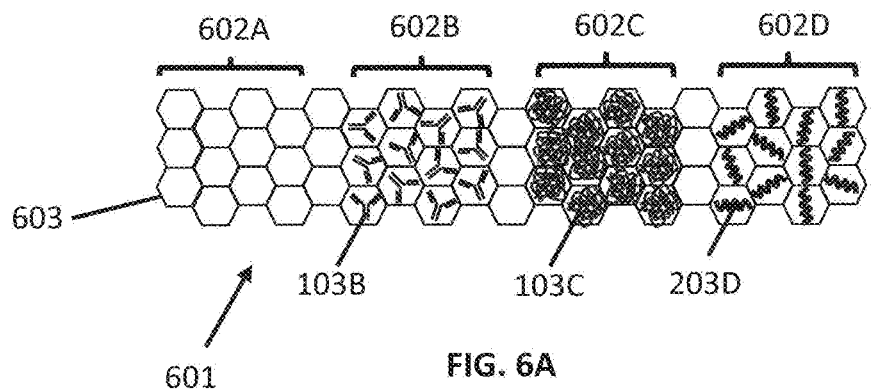
FIG. 6A-FIG. 6C is a schematic depiction of an embodiment of the invention in which multiple biomolecule binder types are coupled to a freestanding porous matrix, which is then registered to specific sensors in the array.
Figure 6B:
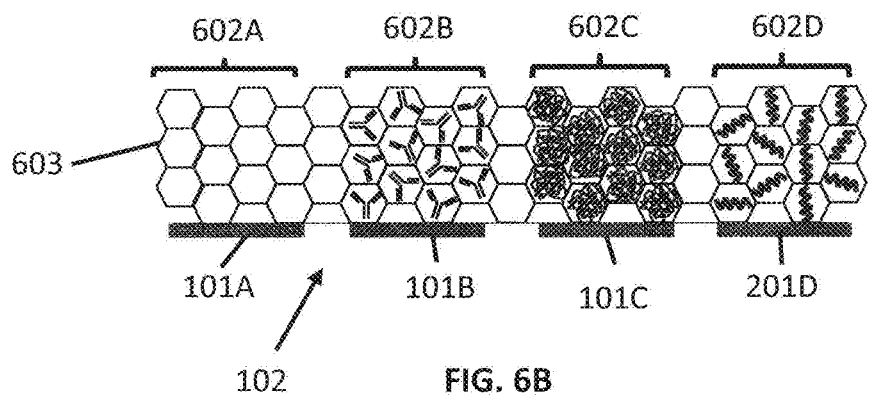
Figure 6C:
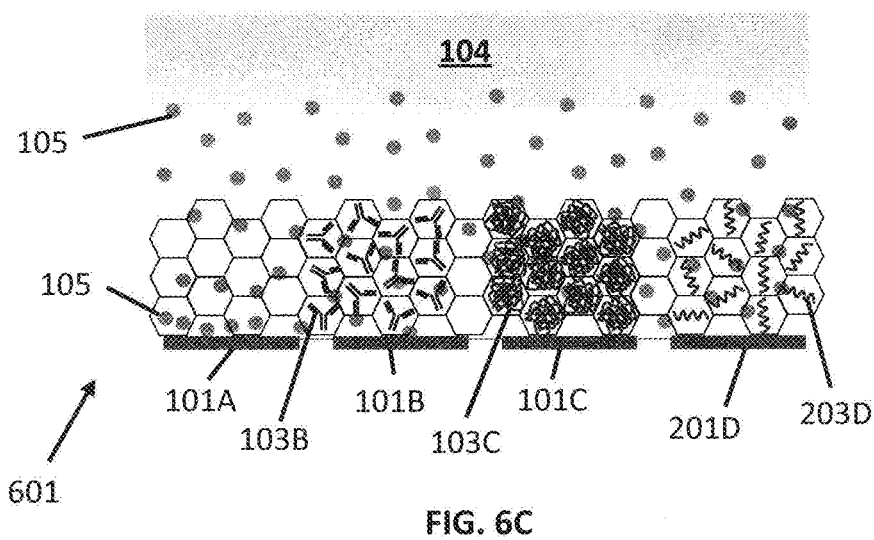

FIG. 6A-FIG. 6C is a schematic depiction of an embodiment of the invention in which multiple biomolecule binder types are coupled to a freestanding porous matrix, which is then registered to specific sensors in the array. In this aspect of the invention, binders are dispensed to freestanding porous matrix 601 that is not initially deposited on sensor array 102 (FIG. 6A). Methods and materials described above in the discussion of FIG. 5 for dispensing, dispersing, and coupling biomolecules to or for directly synthesizing biomolecule binders on deposited porous matrix 501 are also useful with freestanding porous support matrix 601 and structural segments 603. Similarly, the composition of freestanding porous matrix 601 and structural segments 603 may be any of those described above for 501 and 503. In some aspects of the invention, no binders are dispensed to freestanding porous support matrix 601 over select sensor surfaces, as in region 602A of freestanding porous matrix 601.

As schematically depicted in FIG. 6B, freestanding porous matrix 601 comprising binders can be transferred to the surfaces of sensors 101A, 101B, 101C, 201D on sensor array 102. In some embodiments, freestanding porous matrix 601 is registered to sensor array 102 such that specific sensors 101 have selected specific binders 103. For example, region 602B of freestanding porous matrix 601 may receive antibody binders and be registered to sensor 101B. Similarly, region 602C may comprise peptides or protein binders with a specific conformation. Further, region 602D may comprise nucleic acid binders. Sensor array 102 can then be exposed to a solution sample of interrogator ions, either before exposure to a test sample, as shown here in FIG. 6C or after exposure of the sensors to a test sample.

In some embodiments of the invention, binders comprising peptides 103C or nucleic acids 203D may be synthesized in situ on deposited porous matrix 501 that is present on sensor array 102 or on freestanding porous matrix 601. In certain aspects of the invention, synthesized peptides may comprise, at least 2, 3, 4, 5, 6, 7, 8, 9, 10, 15, 20, 25, 30, 35, 40, 45, 50, 60, 70, 80, 90, or 100 amino acids or any number therebetween and inclusive of the smaller and larger sizes listed. In other aspects of the invention, peptide length is not limited and may be any length that can be synthesized on a porous matrix 501 or 601 and that retains functionality as a binder for an analyte. Similarly, in certain aspects of the invention, synthesized nucleic acids may comprise, at least 2, 3, 4, 5, 6, 7, 8, 9, 10, 15, 20, 25, 30, 35, 40, 45, 50, 60, 70, 80, 90, or 100 nucleotides or any number therebetween and inclusive of the smaller and larger sizes listed. In other aspects of the invention, nucleic acid length is not limited and may be any length that can be synthesized on a porous matrix 501 or 601 and that retains functionality as a binder for an analyte. Representative methods for synthesizing peptides and nucleic acids on matrix surfaces can be found in Gao et al., (Proteomics, (2003) 3:2135-2141), and Gao et al., (U.S. Pat. No. 6,426,184).

In some embodiments of the invention, an analyte of interest is a chemical or chemical compound, for example a large macromolecule such as a protein, a carbohydrate, a lipid, or a nucleic acid. Other exemplary chemical analytes include cytokines, hormones, peptides, polypeptides, antibodies, pharmaceutical compounds (e.g., a drug), sugars, acids, bases, or other chemical entities.

In some aspects of the invention, an analyte of interest is a chemical or chemical compound that is not a biomolecule. In other aspects of the invention, the chemical analyte is a biomolecule. As used herein in some aspects of the invention, "biomolecule" refers to a molecule that is produced or capable of being produced in or produced by a living organism. In additional aspects of the invention, a biomolecule is any molecule that is present in or on a living organism. In some embodiments of the invention, a biomolecule is an organic molecule. Exemplary organic biomolecules include proteins, peptides, polypeptides, oligopeptides, amino acids, polysaccharides, nucleic acids, DNA, and RNA. Additional exemplary biomolecules include small molecule metabolites, cytokines, hormones, lipids, antibodies, sugars, acids, bases, and other chemical compounds. In some aspects of the invention, biomolecules may be primary or secondary metabolites, aptamers, or receptors. In additional aspects of the invention, a biomolecule refers to an organic or inorganic degradation product of a biomolecule.

In some embodiments of the invention, a biomolecule analyte may be a cell, a pathogen, a virus, a prion, a fungus, a bacterium, or other organism or a part thereof that can be specifically recognized and sequestered or bound by a binder. In some aspects of the invention, a biomolecule analyte is a fragment of a cell or a cell structure, such as for example only, a region of a cell membrane, a fragment of a cell membrane, a liposome, or a cellular organelle such as a mitochondrion, a nucleus, a Golgi apparatus, or another subcellular structure. A biomolecule analyte may be on or in cell cytoplasm or a subcellular structure.

In additional embodiments of an invention, a biomolecule analyte or "bioanalyte" may be isolated from an organism. In some aspects of the invention, a biomolecule analyte may be purified or partially purified during or following isolation from an organism. Numerous methods for isolating and purifying biomolecules are known to those of skill in the art. It is also contemplated that novel purification methods not yet known in the art could be used for purifying biomolecules for use in embodiments of the invention. In addition, methods for in vitro synthesis of biological small molecules, antibodies, peptides, nucleic acids, cell membranes, membrane mimics, liposomes, and other biological structures are known in the art.

In certain aspects of the invention, analytes are extracted from solid, liquid or gaseous samples. Test and control samples may comprise gases, liquids, and chemical mixtures. A sample may be or may comprise, an extract of an environmental sample, such as for example an air sample or other gaseous sample, a liquid sample, or a soil extract or extract of a water sample. A water sample may contain an analyte that is a biological toxin or toxicant. In some aspects of the invention, test samples are prepared using methods designed to isolate or purify an analyte of interest in a form that will promote formation of an analyte-binder complex. Methods for extracting, isolating, or purifying biological molecules and chemicals from numerous types of samples, including biological, environmental and industrial or pharmaceutical manufacturing samples, are available in the art. In other aspects of the invention, a sample is not purified or extracted prior to contacting the sample with an ion sensor. In certain embodiments of the invention, analytes may be synthetically prepared in vitro. In some aspects of the invention a biomolecule analyte may be synthetically prepared in vitro and not isolated or purified from an organism, cell, or subcellular structure.

In some embodiments, a test sample or control sample comprises individual gases or liquids or mixtures of gases or liquids. In other embodiments, a test or control sample comprises a liquid having a corresponding vapor component.

In some embodiments of the invention, a biological test sample is from an organism. In additional embodiments, test samples are biological samples or extracts of biological samples. In some aspects of the invention, a biological test sample may be from or may comprise blood, serum, plasma, tissue, organs, semen, saliva, breath, tears, sputum, feces, urine, other bodily fluid, hair follicles, skin, or any sample containing or constituting biological cells. Biomolecule analytes for detection and quantification may be released from cell-bearing test samples after in situ cell lysis or be present extracellularly in a sample from a biological organism.

In some aspects of the invention, a biological sample is from a medical, pharmaceutical or biological manufacturing process. In one exemplary aspect of the invention, a sample can be a biological threat sample collected by military or first responders. In still other aspects of the invention, a biological test sample is from a patient. In some aspects of the invention, a sample is from a patient that has tested positive for a disease, a patient undergoing treatment, a patient with a tumor or known mutation that results in the production of a disease-specific analyte, or a patient suspected of having a disease or condition. A biological sample may also include one or more analytes indicative of the presence of a pathogen, a virus, a prion, a fungus, a bacterium, or another organism. In further embodiments, a sample may be collected by sampling ambient air around an object or a subject in order to detect an analyte indicative of a human or other organism or of recent human activity or other activity.

The presence and/or amount of one or more selected analytes in a test sample may be indicative of a disease or condition, may correlate with the severity of a disease or condition, may be used to evaluate the response of a patient to a treatment or may be used to optimize treatment of a patient. The presence or amount of an analyte in a biological sample may also be examined to evaluate and correlate the analyte with pharmacokinetics and to adjust the treatment of a patient such as with a compound or drug. In some aspects of the invention, an analyte may be a metabolic by-product or breakdown product of a treatment compound such as a drug.

In some aspects of the invention, a test or control sample comprises a synthetically prepared biological or chemical analyte. A synthetically prepared biological or chemical analyte may be a precursor or product of a biological, chemical or industrial manufacturing process. Synthetically prepared biomolecules, may be, for example, synthetic nucleic acids or peptides. In specific aspects of the invention, synthetic analytes may be added to a test sample to serve as positive or negative controls for detection or as standards for quantification.

In another exemplary aspect of the invention, the presence and/or amount of an analyte in a test sample may be determined and evaluated for a patient tumor or blood sample prior to the patient being treated or during treatment to determine if there are analytes whose expression and/or concentration correlates with the outcome of the patient. Such determinations can lead to a diagnostic assay that can be used to evaluate tumor and/or blood samples to determine what drug regimen the patient should be provided. In addition, such determinations can be used to identify or select patients suitable for a particular clinical trial. The presence and/or amount of an analyte may be correlated with drug efficacy or drug toxicity that may be relevant to whether that patient is an appropriate patient for receiving the drug or for a particular dosage of the drug. In addition, biological samples from patients with a variety of diseases can be evaluated to determine if different diseases can be identified based on the presence or levels of selected one or more analytes. Some such correlations between biological analytes and specific diseases are known in the art.

Multiple analytes present in a single sample may be queried using methods of the invention. For example, selected individual ion sensors or groups of ion sensors may be derivatized with binders that form binder-analyte complexes with different selected analytes from a single sample. It is contemplated that many analytes can be queried at a single time, in a multiplexed assay format, by using arrays of multiple ion sensors that are derivatized with selected different binders.

The differences in control and test sample ion sensor response profiles observed with different ionic solutions can be used to increase sensitivity of analyte detection and to aid in quantification of an analyte in a test sample. Therefore, in some embodiments of the invention, evaluating a test sample for the presence of an analyte and for quantifying an analyte comprises two stages as illustrated in FIG. 7.

Figure 7:
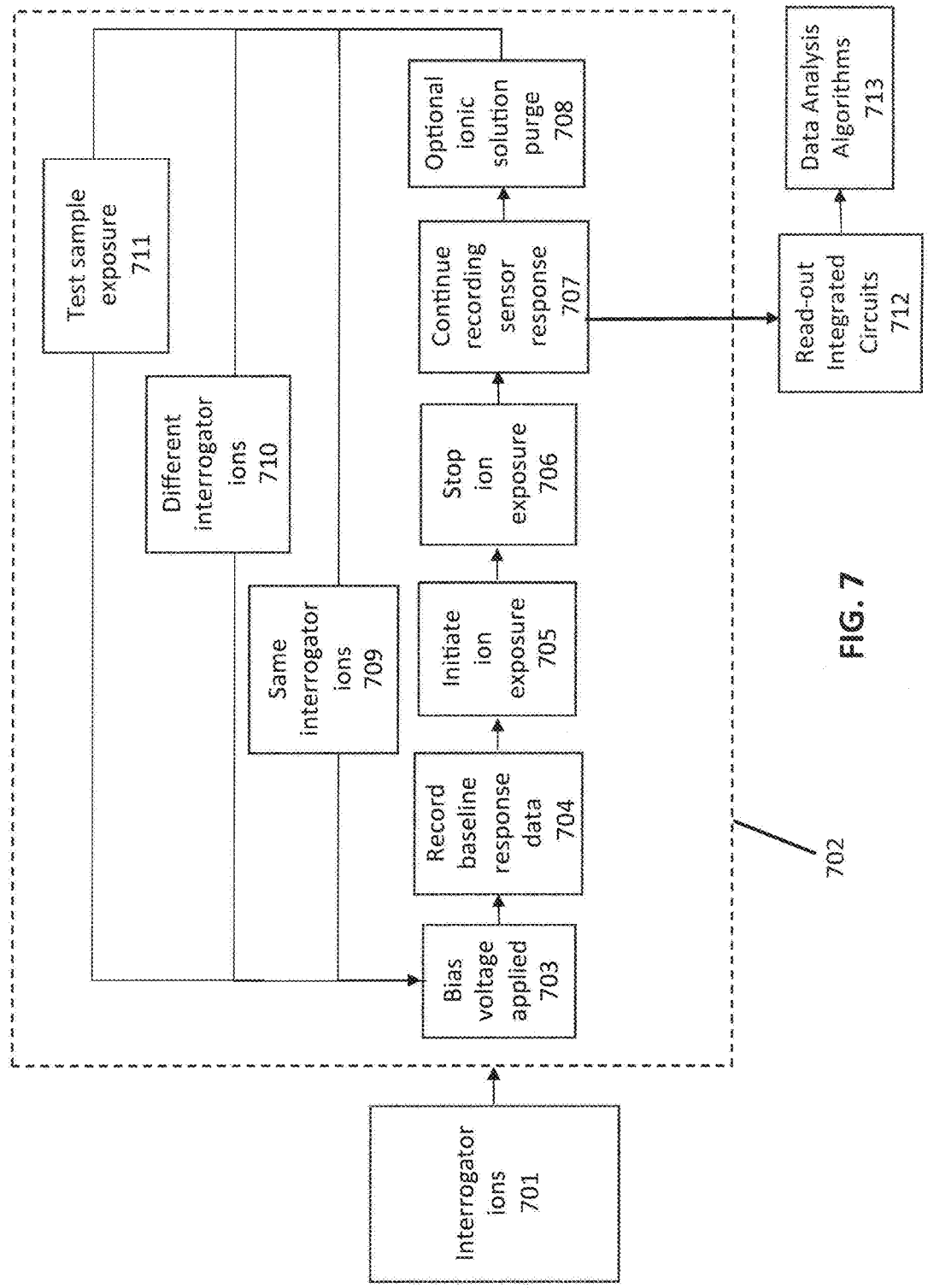
FIG. 7 is a flow chart of an exemplary workflow useful in some invention embodiments for analyzing a test sample to determine the presence or absence of an analyte and for quantifying an analyte in the test sample.

FIG. 7 is a flow chart of an exemplary workflow useful in some invention embodiments for analyzing a test sample to determine the presence or absence of an analyte and for quantifying an analyte in the test sample.

In some embodiments of the invention, evaluating a test sample for the presence of an analyte comprises following a series of test and analysis protocols, testing regimen 702, as illustrated in FIG. 7. In these embodiments, analyte detection and analysis begins by determining a control ion sensor response profile (e.g., 107C) using an ionic solution comprising interrogator ions 701 (e.g., 105) and a sensor (e.g., 101C) having binders (e.g., 103C) on the sensor surface. Determining an ion sensor response profile comprises steps 703 through 707 in FIG. 7 and begins by applying a bias voltage 703 across all sensors 101 in array 102. The bias voltage is applied for a sufficient duration to allow the sensors to stabilize to the environmental conditions (i.e., the sensors exhibit a relatively unchanging current value). After stabilization, determination of baseline response data 704 is initiated. After a selected period of time (typically a few seconds) of determining baseline data, interrogation ion exposure 705 is initiated and continues for a selected period of time prior to stopping the ion exposure 706. Exposure times may range from a few milliseconds to hundreds or even thousands of seconds. It is specifically contemplated that ion exposure times may be for any selected length of time in that range. Sensor response profile data are determined from the selected baseline time point, throughout ion exposure, and after the ion exposure period 707 to the selected end time point. Data determination periods can range from seconds to hours. In some embodiments of the invention, it is specifically contemplated that there is no limit on the time period for data determination. An optional ionic solution purge step 708, such as for example a flow of deionized water over the sensors with or without heating, may be employed to clear ions from the sensors, prior to repeating the process with either the same interrogator ions 709 (e.g., 105) or with different interrogator ions 710 (e.g., 305).

After determining a control sensor response profile with interrogator ions 701, sensors 101 on array 102 are exposed to test sample 711 which may comprise one or more analytes of interest in a variety of concentrations. After exposure of sensors 101 to test sample 711 under appropriate conditions and termination of test sample exposure, test sample sensor response profiles (e.g., 110C) are determined using a separate sample of ionic solution comprising interrogator ions 701 (e.g., 105) and sensors (e.g., 101C) having any binder-analyte complexes (e.g., 109C) that may have formed during incubation with test sample 711. In aspects of the invention, a control sensor response profile is typically performed using the same sensor that will be used for analyzing the test sample; however, the control sensor response profile is determined prior to exposure of the sensor to a test sample 711. As for determination of control sensor response profiles described above, an optional ionic solution purge step 708, such as for example a flow of deionized water over the sensors with or without heating, may be employed to clear ions from the sensors, prior to repeating the process with either the same interrogator ions 709 (e.g., 105) or with different interrogator ions 710 (e.g., 305).

In some aspects of the invention, determining baseline and other sensor response data (i.e., determining an ion sensor response profile) comprises recording the data. In other aspects of the invention, sensor response data are plotted graphically. In still further aspects of the invention, sensor response data are analyzed by ROIC 712 and may be further analyzed with data analysis algorithms 713.

In certain embodiments of the invention, a plurality of ion sensor response profiles is determined for exposure of a sensor to the same interrogator ion sample 709 and may be employed in testing regimen 702. In additional embodiments, one or more determinations of ion sensor response profiles for exposure of a sensor to a different interrogator ion 710 may be employed in testing regimen 702. There is no limit to the number of replicates of testing regimen 702 that may be performed with the same 709 or different 710 interrogator ions.

In various embodiments of the invention, the duration of ionic solution exposure may be varied. By way of example only, ionic solution exposure duration times may be about 0.1 sec, 0.2 sec, 0.5 sec, 1 sec, 2 sec, 5 sec, 10 sec, 20 sec, 30 sec, 60 sec, 120 sec, 300 sec, 400 sec, 500 sec, 1,000 sec, or any duration between 0.1 sec and 1,000 sec or more inclusive. Any ionic solution exposure duration time may be used in combination with any number of replicates performed with the same or different ionic solutions.

In some embodiments of the invention, ion sensor response profiles can be determined at the same time for all ion sensors that are present in array 102, using ROICs 712, such as for example, ROICs comprising silicon CMOS logic. Determination of sensor response profiles provides data for use with analysis algorithms 713 to enable analyte identification and quantification.

In some embodiments, control sensor response profiles are determined using various types and configurations of binders and/or ion sensors. One or more control sensor response profiles and test sample sensor response profiles may be stored in a database, and comparing sensor response profiles comprises comparing one or more test sample response profiles to one or more control response profiles stored in the database. Comparisons of these stored ion sensor response profiles can be used to determine the identity and concentration of one or more analyte in a test sample. In additional aspects of the invention, deconvolution of ion sensor response data enables the identification and quantification of analytes in a test sample.

Qualitative and quantitative differences between the control sensor response profiles (determined with interrogator ions 701 prior to exposure of ion sensors to test sample 711) and the test sample ion sensor response profiles (determined with interrogator ions 701 after exposure of ion sensors to test sample 711) are identified for each sensor employed. Qualitative and quantitative differences and similarities among control sensor response profiles and test sample sensor response profiles can be determined by using ROIC 712 and data analysis algorithms 713 and comparing data from control sensor response profiles with data from test sample sensor response profiles. Numerous computational algorithms are available in the art that are useful for identifying differences in datasets. Such algorithms are applicable for determination of qualitative and quantitative differences between sensor response profiles. In general, quantification of an analyte in a test sample is made by determining the maximum change in sensor response between a control sensor response profile and a test sample sensor response profile determined with the same interrogator ions 709. Quantification of an analyte can be enhanced by comparing control and test sample sensor response profiles determined using additional different interrogator ions 710 and by cross comparison of sensor response profile data from all sensors in a sensor array 102 acquired for each different interrogator ion species 710 using testing regimen 702.

The inventors observed that, upon exposing underivatized sensors (i.e., bare sensors without binders, linkers, a porous matrix, or other molecules, (e.g., 101A as in FIG. 1) to interrogator ionic solutions using testing regimen 702, the determined ion sensor response profiles were different for each type of ionic solution (ions). For use in some embodiments of the invention, sensors lacking binders may be derivatized with linkers 401.

Figure 8:
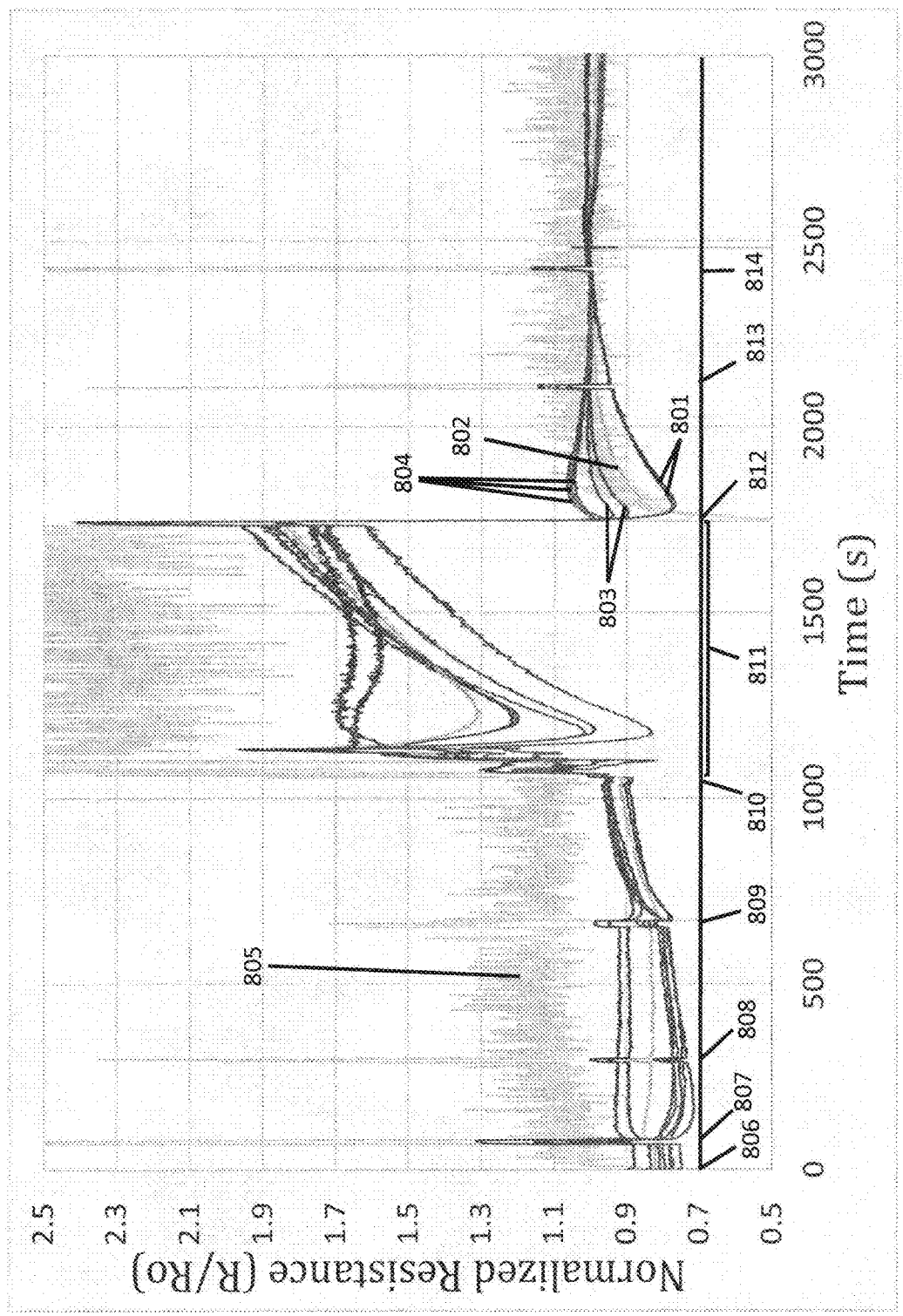
FIG. 8 illustrates sensor response profiles determined, using testing regimen 702, for selected ionic solutions 710 using sensors derivatized with linkers or with binders.

FIG. 8 illustrates sensor response profiles determined, using testing regimen 702, for selected ionic solutions 710 using sensors derivatized with linkers or with binders. For these exemplary demonstrations of sensor operation, the inventors used conductometric semiconducting metal oxide nanotrace sensors. The inventors prepared arrays of semiconducting tin oxide ($SnO_x$) nanotrace sensors, each nanotrace being 80 nm in width, using nanoimprint lithography according to methods described in Savoy et al., U.S. Pat. No. 8,450,131. Sensor response profiles 801 were determined with two linker-derivatized nanosensors (no binder, silane treatment only). Sensor response profile 802 was determined with a sensor that was partially covered with a binder comprising the microRNA miR-122. Two sensor response profiles 803 were determined with sensors that were completely covered with miR-122. Three sensor response profiles 804 were determined with sensors comprising an anti-biotin antibody binder.

The ionic sensor response profiles were determined by measuring the electrical current flowing through the sensors as a function of time. Data collected from the response profile determinations were converted to normalized resistance over time using Ohm's law (V=IR) and the applied bias, typically between 0.01 to 5 V. The voltage was kept low to reduce electrochemical degradation reactions of the electrodes. Response profiles represent individual nanosensor responses and were plotted as the normalized resistance R over the initial resistance $R_0$, which is the average of the first five measurements during time (t)=0 sec through t=~5 sec. In addition to response profiles for nanosensors, the normalized response profile of a sensor containing no intervening tin oxide nanotraces is shown as 805. This sensor measures the current that results from ions 105 diffusing from ionic solution source 104 and interacting with the sensor.

All response profiles were subject to the same fluid contact. Each sensor was initially exposed to an ionic solution containing phosphate buffered saline (PBS) at time (t)=0 sec 806. (For clarity, time points 806-814 are indicated on a separate horizontal timeline above the x-axis and just below the plotted sensor response profiles.) After recording the response profile data in the presence of PBS, the PBS fluid in contact with the sensor array was removed and quickly replaced with a different ionic solution of hybridization buffer at time point 807. Fluid removal caused a sharp increase in the normalized resistance followed by a rapid return when new fluid was added. After adding the different ionic solution, the responses of the different sensors varied. Differences in sensor response were dependent on the type of binder present on a given sensor. Sensors comprising the same binder responded similarly when exposed to ionic solutions, as ions diffused to and interacted with the surface of the sensors. After exchanging PBS with hybridization buffer, sensors without binders demonstrated increased resistances in comparison to sensors with anti-biotin binder, which decreased in resistance but at a slower rate, before stabilizing.

After ~300 sec, time point 808, hybridization buffer was removed from over the sensor and exchanged with the same hybridization buffer at the same concentration. Again, fluid removal caused a sharp increase in normalized resistance followed by a rapid drop to the previous resistance level. Sensor response profiles during the second exposure to the same hybridization buffer ionic solution appeared to follow the same trend as before the solution exchange. At time point 809, sensors were again exposed to PBS buffer, and sensor response profiles exhibited significant changes in parameters. Sensors with the same binder show similar response profiles, and sensors with different binders showed different response profiles.

At t=~1100 sec 810, the fluid over the sensors was exchanged with deionized water, which has a low ionic strength. For this aspect of the experiment, four exchanges of deionized water over the sensor were performed in rapid succession. After the final exchange with deionized water, the sensor response behavior in the time window 811 from ~1100 sec to ~1700 sec illustrated that equilibration of sensor surface-interacting ions led to sensor responses having high resistance values, as expected for a low ionic strength solution. The same observation was made for the sensor having no tin oxide nanotraces 805. Response profile data for the sensor lacking a tin oxide nanotrace is noisier because the overall response magnitude was less because the only current path is the through the ionic solution.

When ionic solution comprising hybridization buffer was re-introduced at time point 812, the sensor resistances fell sharply, but gradually recovered in the following minutes. The rates at which the sensors returned to stable levels varied among sensors having different binder types. Hybridization buffer was exchanged with a fresh sample of the same buffer at time point 813. At time point 814, the sensor array was exposed to an ionic solution containing analyte (test sample). The different sensors responded differently as observed from the plotted sensor response profile data in the time period following 814.

In some aspects of the invention, the inventors observed that exchange of buffer solutions over sensors was accompanied by the introduction of air bubbles, creating unwanted noise in the sensor response profile and delayed interaction of ions with sensors. To reduce this noise, a membrane was inserted between the sensors 101 and ionic solution source 104.

FIG. 9A-9H is a schematic depiction of an embodiment of the invention for detecting analytes, in which an ion permeable membrane is present between ion sensors and an ionic solution source.

Figure 9A:
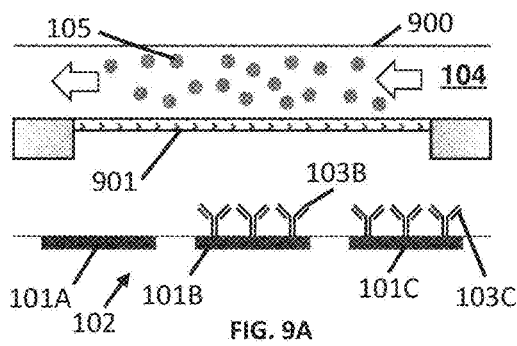
FIG. 9A-9H is a schematic depiction of an embodiment of the invention for detecting analytes, in which an ion permeable membrane is present between ion sensors and an ionic solution source.
Figure 9B:
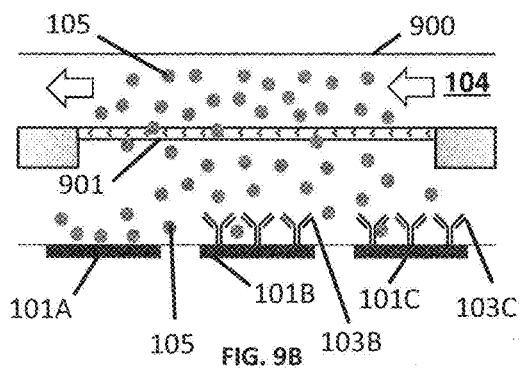
Figure 9C:
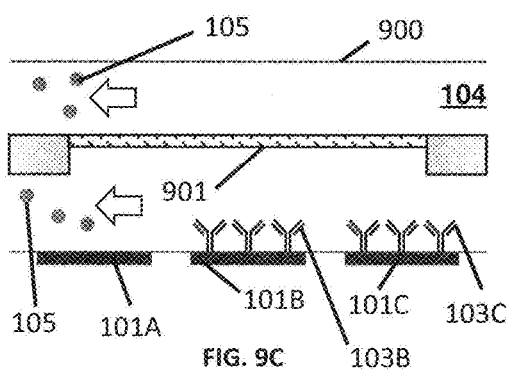
Figure 9D:
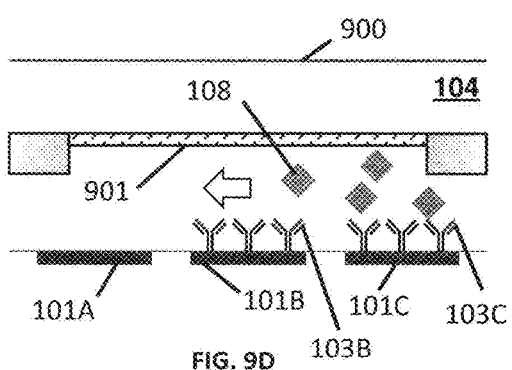
Figure 9E:
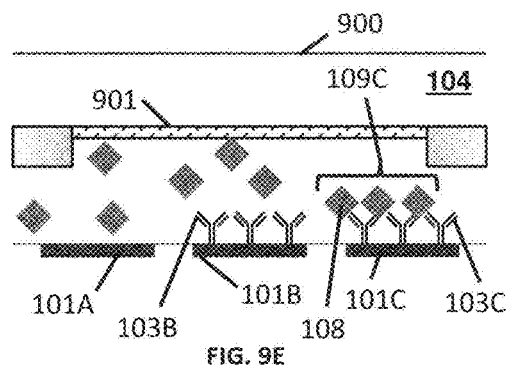
Figure 9F:
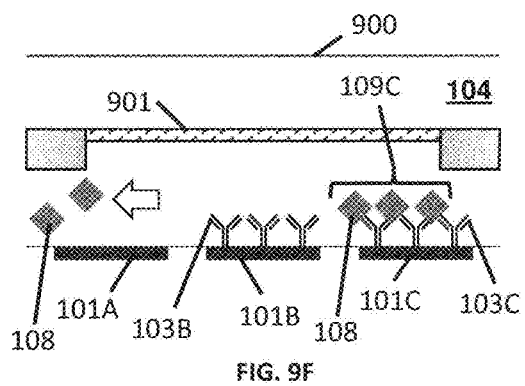
Figure 9G:
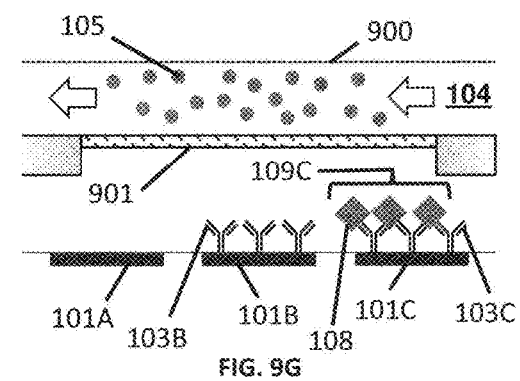
Figure 9H:
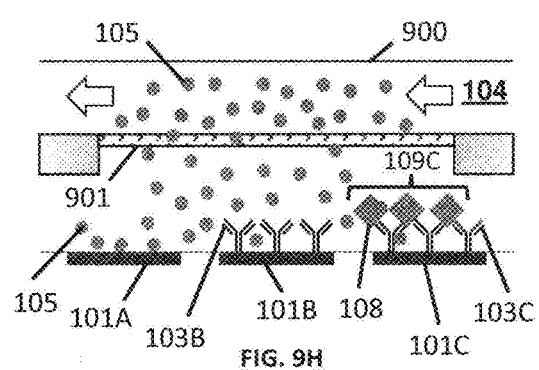

As shown in FIG. 9A, interrogator ions 105 diffusing from ionic solution source 104 enter flow cell 900, which is separated from sensors 101 on sensor array 102 by ion diffusion membrane 901 (For clarity, array 102 is only indicated in FIG. 9A.). Sensors 101, binders 103, ions 105, binder-analyte complex 109C are as described previously for FIG. 1A-FIG. 1E. Interrogator ions 105 diffuse through ion-permeable membrane 901 (FIG. 9B) to sensors 101, and control sensor response profiles 107 (not shown) are determined. FIG. 9C depicts optional ionic solution purge 708, in which interrogator ions 105 are washed from flow cell 900 and sensors 101, following determination of control sensor response profiles. As shown in FIG. 9D and FIG. 9E, sensors 101 are then exposed to a test sample which may comprise analyte 108 that binds selectively to complementary binder 103C on ion sensor 101C forming binder-analyte complex 109C (FIG. 9E). In this example, analytes that would bind to binder 103B on ion sensor 101B are not present in the test sample. FIG. 9F schematically depicts the removal of unbound analytes by a sensor wash step. After exposure of sensors 101 to the test sample, a second sample of interrogator ions 105 diffusing from ionic solution source 104 enter flow cell 900 (FIG. 9G). Interrogator ions 105 diffuse through ion-permeable membrane 900 to sensors 101, some of which comprise binder-analyte complexes 109C (FIG. 9H). Test sample sensor response profiles 110 are determined in the presence of binder-analyte complexes 109C (comprising analyte 108 and binders 103C). Comparing control sensor response profile 107 and test sample sensor response profile, each determined in this manner, enables the detection and quantification of analyte 108 in a test sample. Response profiles may be compared as described previously, using ratiometric, or other principal component data comparison methods well-known in the art.

What is claimed is:

1. A method for determining the presence of an analyte in a test sample, the method comprising the steps of:
   (a) exposing an ion sensor, derivatized with analyte binders capable of interacting specifically with the analyte, to a first liquid ionic solution sample comprising a known interrogator ion species and lacking the analyte;
   (b) stopping sensor exposure to the first liquid ionic solution sample;
   (c) determining a first ion sensor response profile from a selected time prior to initiating sensor exposure to the first liquid ionic solution sample to a selected time after stopping sensor exposure to the first liquid ionic solution sample and during diffusion of the known interrogator ion species to and from the sensor and through the analyte binders;

(d) exposing the sensor to the test sample, under conditions effective for formation of binder-analyte complexes;

(e) terminating exposure of the sensor to the test sample;

(f) after terminating exposure of the sensor to the test sample,
　i) exposing the sensor to a second liquid ionic solution sample, the second liquid ionic solution sample comprising the known interrogator ion species,
　ii) stopping sensor exposure to the second liquid ionic solution sample, and
　iii) determining a second ion sensor response profile from a selected time prior to initiating sensor exposure to the second liquid ionic solution sample to a selected time after stopping sensor exposure to the second liquid ionic solution sample and during diffusion of the known interrogator ion species to and from the sensor; and (g) indicating a presence of the analyte in the test sample if the first and second ion sensor response profiles indicate that diffusion of the known interrogator ion species to and from the sensor and through the analyte binders is different from diffusion of the known interrogator ion species to and from the sensor after terminating exposure of the ion sensor to the test sample.

2. The method of claim 1 wherein the first and second liquid ionic solution samples each comprise a plurality of known interrogator ion species and wherein the known interrogator ion species are the same in the first and second liquid ionic solution samples.

3. The method of claim 1 further comprising comparing the first and second ion sensor response profiles by performing a ratiometric comparison of the profiles.

4. The method of claim 1 wherein the analyte binders are biomolecules.

5. The method of claim 1 wherein the analyte binders are ionophores.

6. The method of claim 1 wherein the analyte is a biomolecule.

7. The method of claim 6 wherein the test sample comprises a biological sample.

8. The method of claim 6, wherein the biomolecule is a biomarker.

9. The method of claim 8, wherein the biomarker is an ion.

10. The method of claim 1 wherein the test sample comprises a liquid.

11. The method of claim 1 wherein the ion sensor is in a sensor array.

12. The method of claim 1 wherein the ion sensor is a conductometric semiconducting metal oxide sensor.

13. The method of claim 12 wherein the ion sensor comprises a plurality of nanotraces made by nanoimprint lithography.

14. The method of claim 13 wherein two or more nanotraces have different widths.

15. The method of claim 1 wherein the analyte binders are attached to the ion sensor with linkers.

16. The method of claim 1 wherein the analyte binders are coupled to a porous matrix.

17. The method of claim 1 further comprising quantifying the analyte.

18. A method for detecting the presence of a plurality of different selected analytes in a test sample, the method comprising:

(a) exposing at least a first ion sensor and a second ion sensor to a first liquid ionic solution sample comprising a known interrogator ion species and lacking at least a first analyte and a second analyte, wherein the first ion sensor is derivatized with selected first analyte binders capable of interacting specifically with the first analyte and the second ion sensor is derivatized with selected second analyte binders capable of interacting specifically with the second analyte;

(b) stopping exposure of the first and second ion sensors to the first liquid ionic solution sample;

(c) determining a first ion sensor response profile from a selected time prior to initiating exposure of the first ion sensor to the first liquid ionic solution sample to a selected time after stopping exposure of the first ion sensor to the first liquid ionic solution sample and during diffusion of the known interrogator ion species to and from the first ion sensor and through the selected first analyte binders;

(d) determining a second ion sensor response profile from a selected time prior to initiating exposure of the second ion sensor to the first liquid ionic solution sample to a selected time after stopping exposure of the second ion sensor to the first liquid ionic solution sample and during diffusion of the known interrogator ion species to and from the second ion sensor and through the selected second analyte binders;

(e) exposing the first ion sensor to the test sample, under conditions effective for formation of first binder-analyte complexes comprising the first analyte and the selected first analyte binders and exposing the second ion sensor to the test sample, under conditions effective for formation of second binder-analyte complexes comprising the second analyte and the selected second analyte binders;

(f) terminating exposure of the first and second ion sensors to the test sample;

(g) after terminating exposure of the first and second ion sensors to the test sample,
　i) exposing the first and second ion sensors to a second liquid ionic solution sample, the second liquid ionic solution sample comprising the known interrogator ion species,
　ii) stopping exposure of the first and second gas sensors to the second liquid ionic solution sample,
　iii) determining a third ion sensor response profile from a selected time prior to initiating exposure of the first ion sensor to the second liquid ionic solution sample to a selected time after stopping exposure of the first ion sensor to the second liquid ionic solution sample and during diffusion of the known interrogator ion species to and from the first ion sensor; and
　iv) determining a fourth ion sensor response profile from a selected time prior to initiating exposure of the second ion sensor to the second liquid ionic solution sample to a selected time after stopping exposure of the second ion sensor to the second liquid ionic solution sample and during diffusion of the known interrogator ion species to and from the second ion sensor;

(h) indicating a presence of the first analyte in the test sample if the first and third ion sensor response profiles indicate that diffusion of the known interrogator ion species to and from the first ion sensor and through the selected first analyte binders is different from diffusion of the known interrogator ion species to and from the first ion sensor after terminating exposure of the first ion sensor to the test sample; and (i) indicating a presence of the second analyte in the test sample if the second and fourth ion sensor response profiles indicate that diffusion of the known interrogator ion species to and from the second ion sensor and through the selected second analyte binders is different from diffusion of the known interrogator ion species to and from the second ion sensor after terminating exposure of the second ion sensor to the test sample.

19. The method of claim 18 wherein the first, second, third, and fourth ion sensor response profiles are stored in a database.

20. The method of claim 19 further comprising determining the quantities of the at least first and second analytes in the test sample.

21. The method of claim 19 further comprising comparing the first and third ion sensor response profiles and comparing the second and fourth ion sensor response profiles using read-out integrated circuits and implementing data analysis deconvolution algorithms.

\* \* \* \* \*

UNITED STATES PATENT AND TRADEMARK OFFICE
CERTIFICATE OF CORRECTION

| | |
|---|---|
| PATENT NO. | : 10,386,365 B2 |
| APPLICATION NO. | : 15/372343 |
| DATED | : August 20, 2019 |
| INVENTOR(S) | : Steve M. Savoy et al. |

It is certified that error appears in the above-identified patent and that said Letters Patent is hereby corrected as shown below:

In the Specification

Column 10, Lines 16-17, "between about one or ten times or more" should read --between about one and ten times or more--

In the Claims

Column 22, Claim 18, Line 47, "ii) stopping exposure of the first and second gas sensors" should read --ii) stopping exposure of the first and second ion sensors--

Signed and Sealed this
Fifth Day of July, 2022

Katherine Kelly Vidal
*Director of the United States Patent and Trademark Office*